United States Patent
Kramer et al.

(10) Patent No.: US 9,645,017 B2
(45) Date of Patent: May 9, 2017

(54) SYSTEM AND METHOD FOR CONDUCTING HEATING, VENTILATION, AND AIR CONDITIONING ANALYTICS

(71) Applicant: Cypress Envirosytems Inc., San Jose, CA (US)

(72) Inventors: Marcus Kramer, San Diego, CA (US); Moses Derkalousdian, San Diego, CA (US)

(73) Assignee: CYPRESS ENVIROSYSTEMS, INC., San Jose, CA (US)

( * ) Notice: Subject to any disclaimer, the term of this patent is extended or adjusted under 35 U.S.C. 154(b) by 277 days.

(21) Appl. No.: 14/678,764

(22) Filed: Apr. 3, 2015

(65) Prior Publication Data

US 2015/0211943 A1    Jul. 30, 2015

Related U.S. Application Data

(63) Continuation of application No. 14/666,585, filed on Mar. 24, 2015, now abandoned, which is a continuation of application No. 13/767,875, filed on Feb. 14, 2013, now Pat. No. 8,992,074.

(60) Provisional application No. 61/600,150, filed on Feb. 17, 2012.

(51) Int. Cl.
| | |
|---|---|
| *G01K 1/00* | (2006.01) |
| *G01K 15/00* | (2006.01) |
| *G01N 25/72* | (2006.01) |
| *G05D 23/19* | (2006.01) |
| *G05D 23/10* | (2006.01) |
| *F24F 11/00* | (2006.01) |
| *G05D 23/02* | (2006.01) |

(52) U.S. Cl.
CPC ............ *G01K 15/00* (2013.01); *F24F 11/006* (2013.01); *F24F 11/0012* (2013.01); *F24F 11/0086* (2013.01); *G01K 1/00* (2013.01); *G01K 15/005* (2013.01); *G01N 25/72* (2013.01); *G05D 23/02* (2013.01); *G05D 23/10* (2013.01); *G05D 23/19* (2013.01); *F24F 2011/0042* (2013.01); *F24F 2011/0052* (2013.01); *F24F 2011/0061* (2013.01)

(58) Field of Classification Search
USPC ..................................................... 374/1, 143
See application file for complete search history.

(56) References Cited

U.S. PATENT DOCUMENTS

| | | | |
|---|---|---|---|
| 7,085,671 B2 | 8/2006 | Fujimoto et al. | |
| 7,137,567 B2 | 11/2006 | Jeffery | |
| 8,069,013 B2 | 11/2011 | Hotton et al. | |
| 2004/0168510 A1 | 9/2004 | Wakahara et al. | |
| 2006/0032245 A1 | 2/2006 | Kates | |
| 2008/0314998 A1* | 12/2008 | Herzon ................ F24F 11/0012 236/1 C |
| 2009/0192653 A1 | 7/2009 | Songukrishnasamy | |
| 2011/0166712 A1 | 7/2011 | Kramer | |

(Continued)

*Primary Examiner* — Mirellys Jagan
(74) *Attorney, Agent, or Firm* — Manuel de la Cerra

(57) ABSTRACT

A system and method for conducting heating, ventilation, and Air Conditioning Analytics is disclosed. The system uses one or more wireless pneumatic thermostats (WPT) and/or various other sensors in communication with a control device to maintain, troubleshoot, calibrate, optimize, or otherwise adjust an installed pneumatic HVAC system.

18 Claims, 8 Drawing Sheets

(56) References Cited

U.S. PATENT DOCUMENTS

| | | | | |
|---|---|---|---|---|
| 2014/0376586 A1* | 12/2014 | Dawson | ................ | G01D 18/00 |
| | | | | 374/1 |
| 2016/0370799 A1* | 12/2016 | Denton | .............. | G05B 23/0243 |
| 2017/0023269 A1* | 1/2017 | Gevelber | ............. | F24F 11/0001 |

* cited by examiner

SYSTEM AND METHOD FOR CONDUCTING HEATING, VENTILATION, AND AIR CONDITIONING ANALYTICS

1.0 CROSS-REFERENCE TO RELATED APPLICATION

This application is a continuation application U.S. patent application Ser. No. 14/666,585, filed on Mar. 24, 2015, which is a continuation application of U.S. patent application Ser. No. 13/767,875, filed Feb. 14, 2013, now U.S. Pat. No. 8,992,074 issued on Mar. 31, 2015, which is the non-provisional of U.S. patent application Ser. No. 61/600,150 filed on Feb. 17, 2012. All of these applications are incorporated herein by reference.

2.0 FIELD OF THE INVENTION

The present disclosure relates generally to systems which monitor pneumatic control devices and systems, and more particularly to control devices, systems, and methods for controlling, monitoring, and diagnosing pneumatic devices, and the like.

3.0 BACKGROUND OF THE INVENTION

Pneumatic-based control devices may control various systems based on a gas flow or pressure. Typically, such pneumatic control devices may include a "flapper" technology that may regulate a gas flow to thereby provide a pneumatic control signal.

One example of a pneumatic control device is a pneumatic thermostat. Pneumatic thermostats may be used as sensing and control devices for pneumatically-controlled devices, such as variable air volume (VAV) units, ventilators, fan coil units, reheat coils, radiators, and the like, typically employed in a heating, ventilation, and air conditioning (HVAC) system.

One type of pneumatic thermostat includes a pneumatic temperature controller, a setpoint cam, and a knob/slider. Such a pneumatic temperature controller may be a combination of a valve unit (typically a diaphragm-type valve), a "flapper" controlled nozzle, and a bimetallic strip. Supply air is passed through the valve unit which controls the pressure at an outlet, after allowing a portion of the supply air to exit into the atmosphere through the flapper-controlled nozzle. The outlet pressure can be used to pneumatically control another device.

Changes in the position of a flapper over the control nozzle may create corresponding changes in the amount of supply air exited to the atmosphere. This, in turn, may change the outlet air pressure.

A setpoint for such a pneumatic temperature controller may be manually set, by adjusting a cam position using a knob or slider. Adjusting the cam position may change the amount of force applied by the bimetallic strip to the flapper. The position of the flapper may thus be determined by a resulting balance between by the force exerted from the portion of supply air passing through the nozzle on one side, and the force generated by the bimetallic strip on another side. The force generated by the bimetallic strip may be proportional to the difference between the setpoint and the ambient temperature for the pneumatic thermostat.

In the above arrangement, when the ambient temperature is at the setpoint, the flapper may reach an equilibrium position, creating a certain clearance above the nozzle, which in turn creates a corresponding outlet pressure. However, when the ambient temperature is away from the setpoint in one direction, the bimetallic strip exerts less force on the flapper. This may move the flapper away from the nozzle, increasing the clearance between the flapper and nozzle. Such increased clearance may allow more supply air to escape to the atmosphere, reducing the outlet pressure. Conversely, when the ambient temperature is away from the setpoint in the other direction, the bimetallic strip exerts greater force on the flapper. This may move the flapper closer to the nozzle, decreasing the clearance between the flapper and nozzle. Such decreased clearance results in less supply air escaping to the atmosphere, increasing the outlet pressure.

HVAC control systems which incorporate wireless pressure thermostats are known in the art. FIG. 7 depicts a system incorporating wireless sensors (730-0, 730-1, 730-3, 748-0, 748-1, 748-2) which communicate through wireless relays (734-0, 734-1) to a system controller (732). The information from the system controller (732) can be accessed and displayed on a variety of electronic devices (738, 740, 744, 745). U.S. Published Patent Application 2009/0192653 discloses just such a system and the entirety of that application is incorporated herein. U.S. Published Patent Application 2011/0166712 discloses apparatuses and methods of deadband setpoint control of pneumatic controllers and is incorporated herein in its entirety. These applications, however, are silent on how the sensor data is processed to maintain, troubleshoot, calibrate, optimize, or otherwise adjust an installed pneumatic HVAC system.

Therefore, there exists a need to marshal the data generated from a network of pneumatic thermostats, and for analytical methods performed on that data to examine that data to provide answers to HVAC system health, performance, and response, as well as identifying the precise cause of non-ideal system performance. Moreover, there exists a need for this data compilation and for analyses over time and correlated/compared to the data compiled from the various zones within the pneumatic thermostat network.

4.0 SUMMARY OF INVENTION

The present application provides a novel apparatus and system for conducting analytics on an HVAC system and self-diagnosing problems. The novel HVAC system has at least one pneumatic thermostat having a pressure sensor on a branch pressure line and an ambient temperature sensor. Those sensors are connected to processors configured to perform several steps, including recording the ambient room temperature from the temperature sensor, recording the branch line pressure from the pressure sensor, and recording the setpoint value. The processor changes the setpoint value, and the pressure, temperature and setpoint values are again recorded, and this is repeated for a plurality of setpoint values. The processor calculates an expected pressure based on the recorded setpoint value and recorded ambient room temperature, and analyzes the difference between expected pressure and recorded pressure in order to determine if the thermostat is behaving as expected. When the thermostat is not behaving as expected, the system signals an alert and compensates for the unexpected behavior. The processor may also calculate compensation commands to correct the unexpected behavior, and those commands may be new setpoint values.

The processor may further include determining a first trend in the recorded pressures at various recorded ambient temperatures and determining a second trend in expected pressures at various recorded ambient temperatures. The system identifies the thermostat as having an incorrect control action when the first trend is substantially opposite to the second trend.

The processor may further include setting a throttle slope tolerance, and determining a recorded pressure slope based on the recorded pressures. The system identifies the thermostat as having an errant throttle slope when the recorded pressure slope falls outside of the tolerance.

The processor may further include setting an ambient temperature error tolerance and setting a throttle slope error tolerance based on the expected magnitudes of the change of the pressures. The processor sets a throttle slope error tolerance, and determines a recorded pressure slope based on the recorded pressures. The system identifies the thermostat as having a stuck actuator when both of the following occur: the recorded ambient temperatures differ from the recorded setpoint values by more than the ambient temperature error tolerance; and the recorded pressure slope falls within the throttle slope error tolerance.

Other systems, methods, features and advantages of the invention will be or will become apparent to one with skill in the art upon examination of the following figures and detailed description. It is intended that all such additional systems, methods, features and advantages be included within this description, and are within the scope of the invention.

5.0 BRIEF DESCRIPTION OF THE FIGURES

The foregoing and other aspects, objects, features and advantages of the method and system disclosed will become better understood with reference to the following description, claims, and accompanying drawings, where:

6.0 DETAILED DESCRIPTION

The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in a simple block diagram format in order to avoid unnecessarily obscuring the present invention. Thus, the specific details set forth are merely exemplary. Particular implementations may vary from these exemplary details and still be contemplated to be within the spirit and scope of the present invention.

References in the description to "one embodiment" or "an embodiment" means that a particular feature, structure, or characteristic described in connection with the embodiment is included in at least one embodiment of the invention. The appearances of the phrase "in one embodiment" in various places in the specification do not necessarily all refer to the same embodiment.

Various embodiments will now be described in detail that show devices, systems and methods that include a control device that may include a non-electrical control section that may interface with legacy non-electrical control system connections. At the same time, such a control device may provide wireless control and monitoring.

Control devices described herein may be compatible with existing site connections to enable rapid replacement of legacy control devices. In particular examples, control devices may be wireless pneumatic thermostat (WPT) devices that may replace existing manually-controlled pneumatic thermostats.

Figure 8:
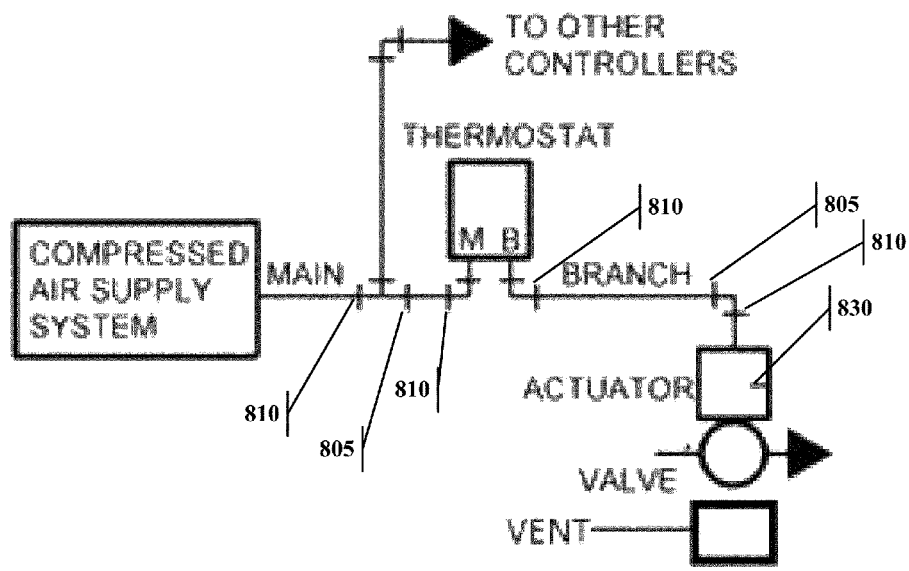
FIG. 8 is an illustration for a pneumatic thermostat system.

FIG. 8 depicts a pneumatic thermostat 800 that controls a heating or cooling system via a series of air-filled control tubes. The pressure lines from the pressurized air source, i.e., a compressor, is called the main pressure line, and the lines after the thermostat to actuators are called the branch lines. Each of the main and branch pressure lines can incorporate pressure regulators 805 to maintain desired pressure within each in the lines. Pressure sensors 810 may be installed before and after each regulator 805 to verify the proper operation. This "control air" system responds to the pressure changes (due to temperature) in the control tube to activate heating or cooling when required. The control air typically is maintained on "mains" at 15-18 psi (although usually operable up to 20 psi). Pneumatic thermostats typically provide output/branch/post-restrictor (for single-pipe operation) pressures of 3-15 psi which is piped to the end device (valve/damper actuator/pneumatic-electric switch, etc.). A direct acting (DA) pneumatic thermostat increases branch line pressure as temperature increases. A reverse acting (RA) pneumatic thermostat decreases branch line pressure as temperature increases. The amount of change in temperature that is required to boost the output pressure of the pneumatic thermostat branch line from 3 to 13 PSI (full closed to full open) is called the proportional band or the throttling range. Normally, a pneumatic thermostat throttling range is set from 2 to 6 degrees. For operation of a pneumatic thermostat a temperature change in the room creates a pressure change in the line which triggers operation of one or more actuators which open or close vents to adjust the current room temperature to the desired value. The system may also incorporate one or more actuator position sensors 830 which can communicate the current position of the actuators back to the central controller.

Figure 9:
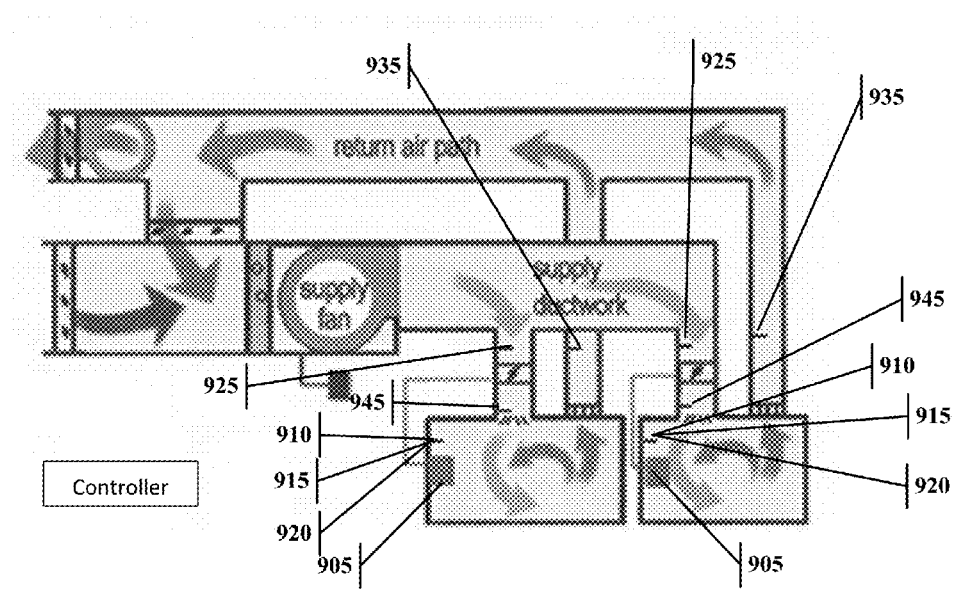
FIG. 9 is an illustration of an embodiment of the HVAC control system.

FIG. 9 depicts an embodiment of a HVAC system employing various sensors to perform the analytics as disclosed in the present application. The systems may incorporate one or more thermostats 905 which may be wireless pneumatic thermostats (WPT) which communicate information back to a central controller 930. The system may incorporate one or more audio transducer/microphones 910, one or more room occupancy sensors 915, and/or one or more ambient light sensors 920. The audio 910, occupancy 915, and ambient light 920 sensors may be wired or wireless and communicate the information back to the central controller 930. While depicted at a single location, the audio 910, occupancy 915, and ambient light 920 sensors may be stand-alone sensors and may be located in various area of a room as required. The system may also contain one or more airflow sensors for the pressure side 925 and return side 935. The airflow sensors can communicate information back to the central controller 930. Airflow sensors 945 may be located at the vents for the pressure side to determine the airflow just prior to entering a room. The airflow sensors may have various other sensors incorporated within, such as particle detectors, chemical/biological agent detectors, radiation detectors, carbon monoxide detectors, or humidity sensors, depending on the system requirements. The exact placements of the sensors in FIG. 9 is notional and in no way limiting, as each system can include sensors based on the system design requirements. The system does not need to have all of these sensors to implement each of the methods described below.

6.1 Detection of Calibration Offset Error

Since there is a mechanical component to pneumatic thermostats, it is common for them to require periodic calibration, especially during installation. The calibration procedure adjusts the thermostat to the neutral pressure when the setpoint and ambient temperatures match. Neutral pressure is the pressure at which there is no heating or cooling. It is the balance point between heating and cooling in a dual system, or it is simply the end-point when heating or cooling stops in a single system.

The theoretical neutral pressure is determined by viewing the specifications of the HVAC actuator for the zone (typically the spring rates). A dual system that has a cold water valve with a spring rate of 3-8 psi and a hot water valve with a spring rate of 8-13 psi would have a theoretical neutral pressure of 8 psi. If the mechanical components are out of specification tolerance in any way, then this actual neutral pressure can be something other than 8 psi.

It is rare that building maintenance technicians follow the periodic calibration schedule. Moreover, the calibration procedure for most pneumatic thermostats is also very sensitive, so it is very error prone. It is desirable to have the electronic control system automatically calibrate its control loop and/or the mechanics of the thermostat.

The WPT controller or the central system controller monitors setpoint, branch pressure, ambient temperature, and throttle slope over time to calculate the offset. By monitoring and comparing multiple zones, the controller can make more intelligent decisions about calibration corrections and can distinguish them from behavior that indicates malfunctioning or improperly-configured equipment. By characterizing the throttle slope of the WPT, the throttle range of the WPT, and the spring range of the actuator for each zone, the controller can perform the calibration procedure with no human input at all. In order to correct any detected calibration error/offset, the controller introduces a correction offset to the setpoint control command.

The first step in this process is to calibrate to a theoretical neutral pressure. The theoretical thermostat pressure response to ambient pressure changes given a selected setpoint temperature and an assumed neutral pressure is governed by the following equations:

For a Direct Acting Case:

THEORETICAL_BRANCH_PRESS=((AMBIENT_TEMP−SETPOINT_TEMP)*THROTTLE_SLOPE (psi/f))+NEUTRAL_PRESS    (Eq. 1)

For a Reverse Acting Case:

THEORETICAL_BRANCH_PRESS=((SETPOINT_TEMP−AMBIENT_TEMP)*THROTTLE_SLOPE (psi/f))+NEUTRAL_PRESS    (Eq. 2)

The controller calculates the theoretical branch pressure for several historical data points. It is helpful to select data points that are relatively stable (small ambient temperature change between the prior interval and the current interval, such as less than one degree Fahrenheit) to avoid introducing artifacts from highly dynamic environmental situations. It may also be preferable to only select data points where the ambient temperature matches the setpoint temperature. This may prevent any uncertainty in the throttle slope from affecting the calibration correction.

The controller then calculates an average of the difference between the theoretical branch pressures for those data points and the actual branch pressures measured.

CALIBRATION_OFFSET_PRESSURE=(SUM(THEORETICAL_BRANCH_PRESS)/NUM_SAMPLES)−(SUM(ACTUAL_BRANCH_PRESS)/NUM_SAMPLES)    (Eq. 3)

CALIBRATION_OFFSET_TEMPERATURE=CALIBRATION_OFFSET_PRESSURE*(1/THROTTLE_SLOPE (psi/f))    (Eq. 4)

This average delta of either temperature or pressure units calculated using the equations above can then be used to adjust any future setpoint change commands or simply to modify the direct proportional-integral-derivative (PID) control loop of an electro-pneumatic thermostat.

The next step is to calibrate to the actual neutral pressure. The first step in this calibration process is to determine the actual spring rate of the HVAC actuator for each zone. Once the actual spring rate of the HVAC actuator for each zone is determined, the assumed neutral pressure should be replaced with the actual measured neutral pressure. In this way, an installer need not worry about specifying the wrong neutral pressure during the initial installation and calibration process. The WPT can completely calibrate itself to each HVAC zone, even if each one has different actuator equipment.

In one embodiment, the system may be calibrated using the actual throttle slope. Section 6.5 describes how to determine the actual throttle slope of the thermostat. This method can be followed to substitute the actual throttle slope into the equations in the prior section instead of using the theoretical throttle slope. This will eliminate the need to only select historical data points where the setpoint is equal to the ambient temperature, since now the throttle slope is known. Even if the setpoint is several degrees away from the ambient, the theoretical Branch_Pressure can be accurately calculated knowing the Throttle_Slope (as in the equations above).

Another method to identify zones that are out of calibration is to compare multiple neighboring zones or even all zones in a building. The central wireless controller processes historical data for the desired set of zones. The controller calculates the average delta between theoretical and actual branch pressure as shown earlier (Eq. 3). The controller then identifies outliers from this set of thermostats, even if all of them have a nonzero offset. It is possible that the theoretical neutral pressure or the theoretical throttle slope is incorrect, which would yield an offset from the prior equation (Eq. 3 and 4). The controller uses a histogram method (or similar) to identify outliers.

For example, in a set of ten thermostats, if eight of them have a calibration offset pressure of 1 psi from Eq. 3, and one has an offset of 2 psi, and another of 4 psi, it is easy to determine that the 4 psi thermostat is likely out of calibration, and the 2 psi thermostat may be out of calibration. It is less likely that all eight of the remaining thermostats are out of calibration, but it is still possible if the installers miscalibrated all of the thermostats in the same way to yield the 1 psi offset.

The controller can use the results of this histogram analysis to determine which zones (i.e., thermostats) to apply a correction to (based on an error magnitude threshold), or it can simply alert maintenance personnel and associate a severity of the calibration error based on the magnitude of the outliers (outside the standard deviation) in relation to the baseline.

6.2 Detection of Control Action

By monitoring zone branch pressure response to an ambient temperature change over time, the thermostat action, direct or reverse, can be determined. Direct-acting thermostats have a pressure increase in response to a temperature increase. Reverse-acting thermostats have a pressure decrease in response to a temperature increase. This can apply to both a conventional pneumatic thermostat body, or to an electro-pneumatic solution (direct control of pressure feedback loop by electronics). In the electro-pneumatic case, perhaps the installer configured the thermostat for the incorrect behavior. For the conventional case, the installer may have installed the wrong thermostat for the zone or the installer may have installed the wrong actuator, such as a normally open valve versus a normally closed valve.

The monitoring system can use the pressure and temperature response to determine if the wrong thermostat was installed or if a variable air volume (VAV) or reversing valve is misconfigured. This information is also useful when other zone diagnostics are being performed.

Figure 1:
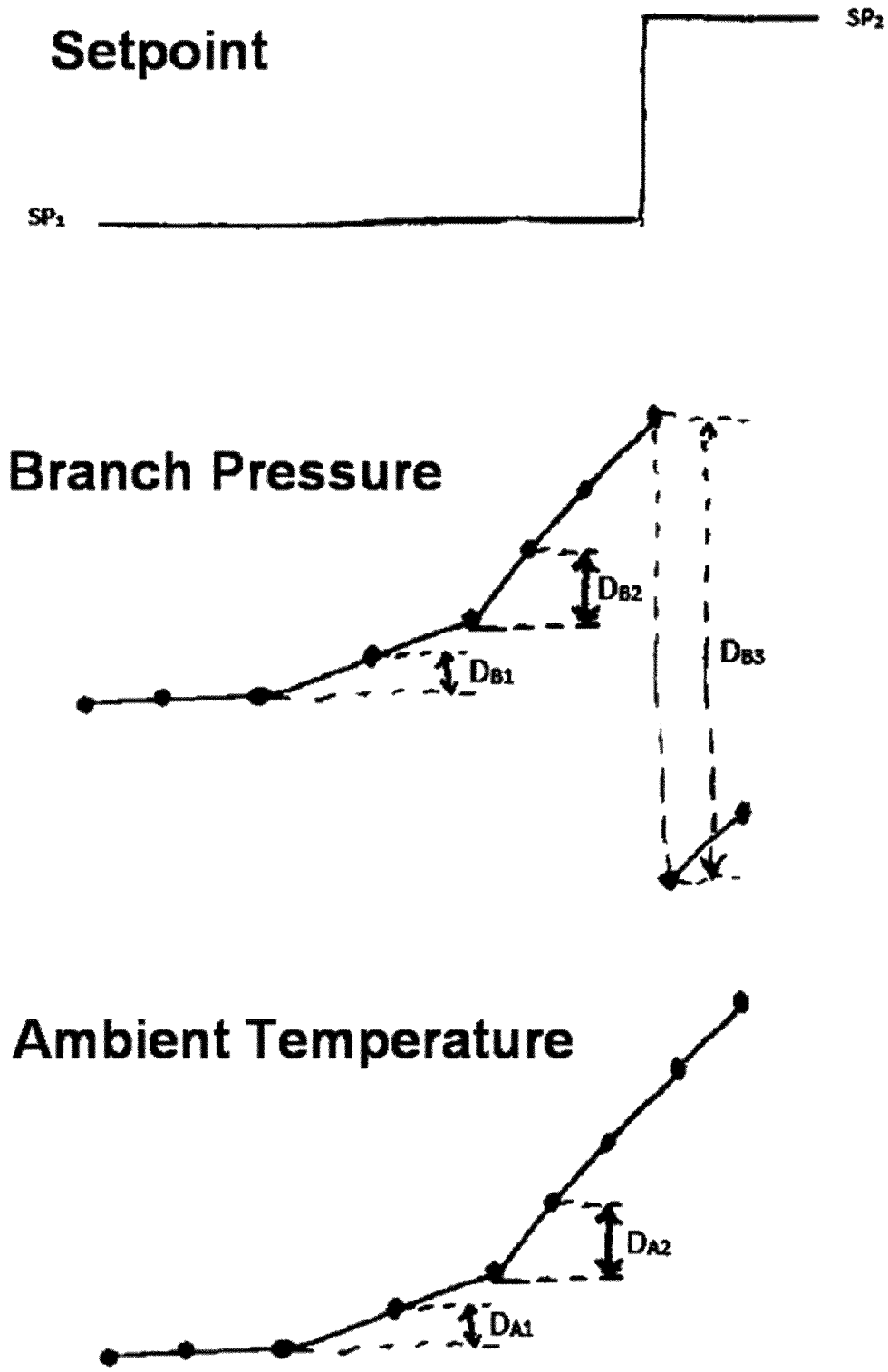
FIG. 1 illustrates the collection of pressure and temperature samples from a particular zone for analysis.

A data aggregator or server may collect pressure and temperature samples from a particular thermostat or zone for analysis as depicted in FIG. 1. In another embodiment, each zone may contain a microprocessor which collects pressure and temperature samples and performs the analysis locally.

The following describes one method for detecting action. This method will detect bi-metallic strip action rather than lever arm action. A bi-metallic strip can be defined as any mechanism which adjusts branch pressure in response to temperature change. One example can be a bi-metallic strip, another can be a electromechanical device, and another can be an electronic device with or without an electro-pneumatic control system.

Figure 2:
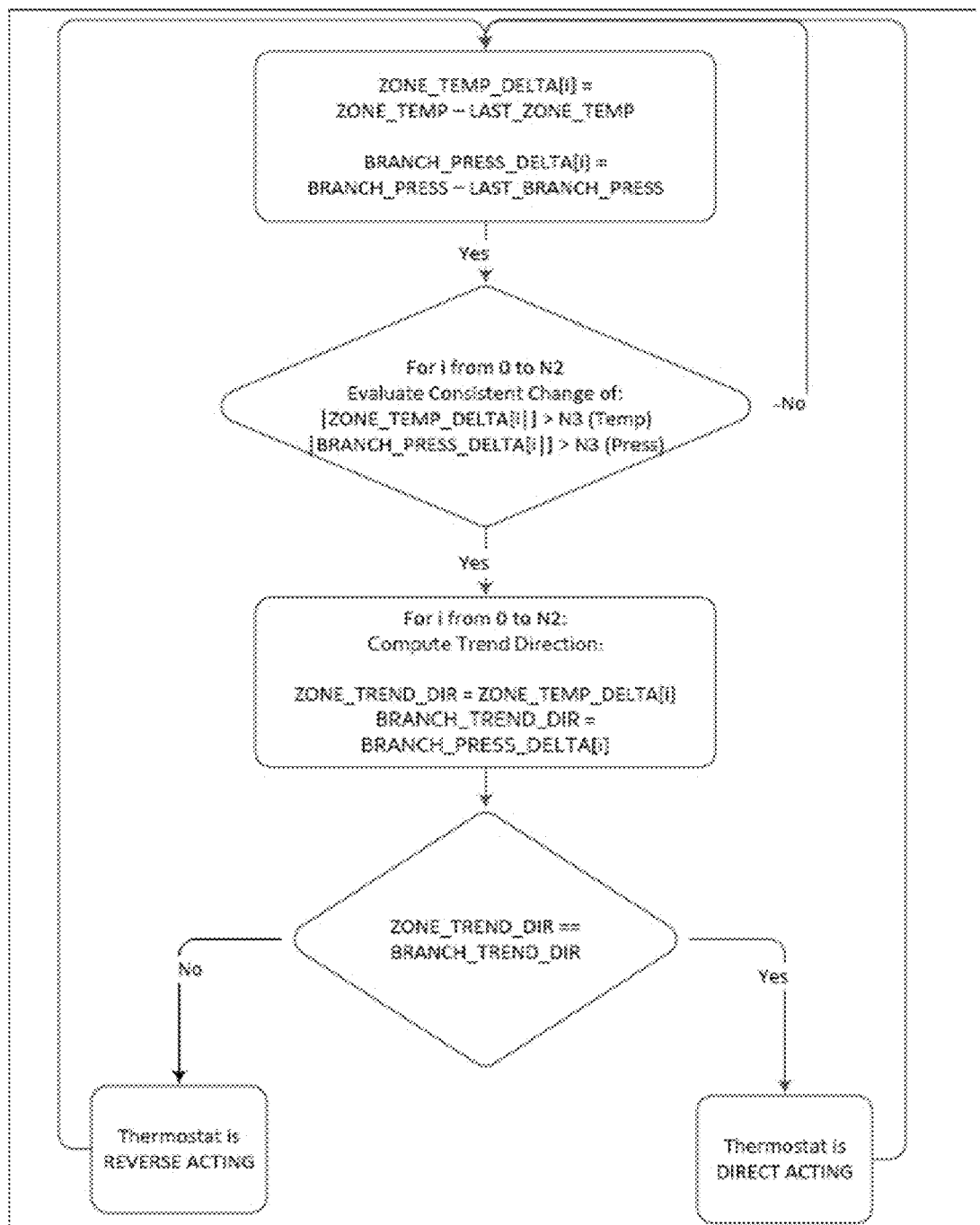
FIG. 2 illustrates a flowchart for one method for detecting action.

This method for detecting action is depicted in FIG. 2. The relative change or delta between N1 subsequent samples of branch pressure and ambient zone temperature can be calculated. Once the deltas are calculated, they can be analyzed for consistent change in a single direction. Optional filters can be applied during this step to ignore minor fluctuations in the delta trend. The delta trend can be analyzed using one of several different methods. One example would be a sliding window evaluation where the minimum and maximum values within a given window are used to determine direction and magnitude. Another method would count the number of deltas for each direction within a given window. Once a window of N2 delta samples containing a consistent directional trend of magnitude N3 for both the branch press and ambient temperature has been detected, the action can be concluded.

A direct-acting thermostat is detected if the consistent change detected above is always in the same direction for both the branch pressure and ambient temperature. A reverse-acting thermostat is detected if the consistent change detected above is always in opposite directions for the branch pressure and ambient temperature.

The algorithm described above contains several optional thresholds, N1, N2, and N3, which can be adjusted to prevent false results.

In another approach, branch pressure and ambient temperature samples can be applied to any well-known regression-style line-fitting algorithm to extract overall trends. The trends rather than the raw samples can then be processed in a manner similar to that described above to determine action.

Both branch pressure and ambient temperature are naturally noisy. It is desirable to eliminate such noise to analyze overall delta trends properly. One option would be to apply any number of well-defined filters to the branch pressure and ambient temperature samples before analyzing trends. Another option would be to apply well-defined regression-type trend line to extract the overall direction of the delta.

It is important to note that any change in branch pressure resulting from a setpoint change must be ignored for the purposes of determining a thermostats action. If the throttle slope of the thermostat under analysis is known, any branch pressure change introduced as a result of setpoint change can be reversed or eliminated mathematically in order to calculate the relative change of pressure to determine action as described above. The equation below shows one way of performing this correction.

NORMALIZED_BRANCH_PRESS (Direct Acting)=
BRANCH_PRESS+((SETPOINT (f)−70 f)/(1/
TROTTLE_SLOPE (psi/f))) (Eq. 5)

NORMALIZED_BRANCH_PRESS (Reverse Acting)=BRANCH_PRESS−((SETPOINT (f)−70
f)/(1/TROTTLE_SLOPE (psi/f))) (Eq. 6)

If the main pressure is also monitored, any branch pressure changes resulting from fluctuations in the main pressure can also be canceled out. In another approach, the algorithm described above can ignore samples during which time the main pressure is fluctuating or the setpoint is changing.

Another method can use a temporary setpoint change and branch pressure response to detect the action of a thermostat. This method will detect lever arm action rather than bi-metallic strip action as described above. The lever arm can be defined as any mechanism in a thermostat that adjusts the branch pressure based on a setpoint change or a direct electronic control input to alter branch pressure. One example is a lever arm which can be mechanically adjusted to change the setpoint, another example can be a level arm which is actuated electromechanically and another example can be a level arm which is actuated electronically. A setpoint change can be sent to a particular zone. The change can be sent at any time for any length of time. For tenant comfort, the change can ideally be sent during unoccupied periods. Once the change is sent, the branch pressure response is monitored. If the branch pressure increases as a result of an increase in setpoint change, the lever arm action is reverse acting. If the branch pressure decreases as a result of an increase in setpoint change, the lever arm action is direct acting. The setpoint can be changed in either direction as long as the resulting logic is appropriately adjusted.

In addition to determining the action of a particular zone using the methods described, a decision can be made on whether or not that action is appropriate for its zone. It is very common for a thermostat with one action to be installed in a zone expecting a different action. In such a situation the thermostat will drive the zone temperature in the opposite direction. For example, if the zone temperature has increased above the setpoint, an incorrect acting thermostat will call for additional heating instead of cooling, causing the zone temperature to further increase. In one embodiment, the correctness of a thermostat's action can be determined by monitoring the ambient zone temperature, setpoint, and branch pressure.

Figure 3:
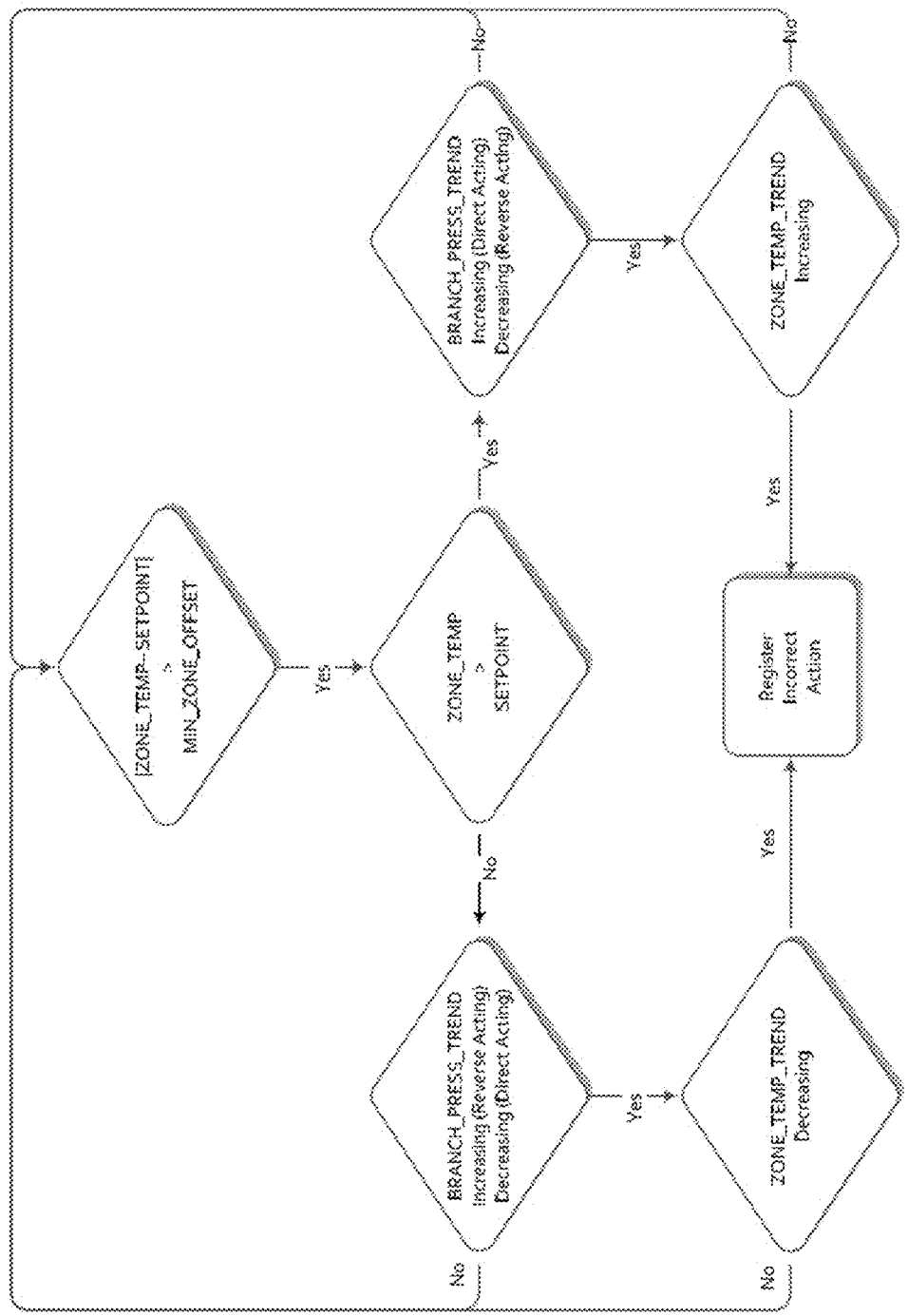
FIG. 3 illustrates a flowchart for one method for determining the correctness of a thermostat's action by monitoring the ambient zone temperature, setpoint, and branch pressure.

FIG. 3 depicts a flowchart for detecting action correctness using a trending-based algorithm. Using methods similar to those described above, the trends of both zone temperature and branch pressure can be monitored. The zone temperature can be compared against the setpoint and evaluated for a change larger than some minimum offset. When a zone temperature change is detected, the algorithm can continue to analyze the trend. If the branch pressure trend is responding to this change but the zone temperature trend continues to drift farther away from setpoint, the zone can be registered as containing an incorrect-acting thermostat. If the branch pressure is not responding, the cause of the zone temperature change is unknown and correctness of action cannot be determined. If the zone temperature trend starts to drift towards the setpoint, the zone can be registered as containing a correct-acting thermostat. The above algorithm can be enhanced by including exterior temperature as well as neighboring zone temperature as inputs to eliminate or account for their influence. The zone temperature trend can be adjusted to isolate only changes caused by the supply air temperature.

Figure 4:
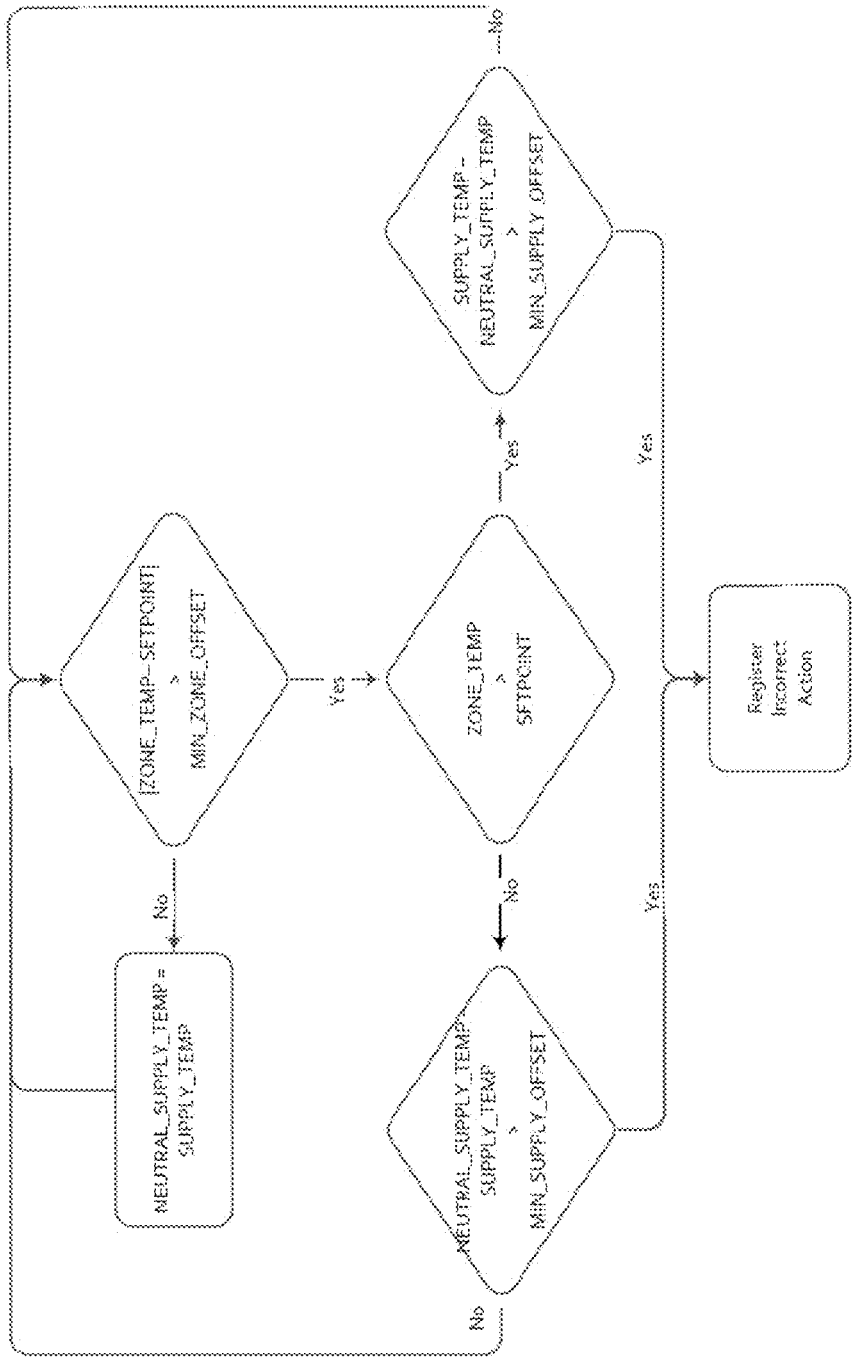
FIG. 4 illustrates a flowchart for detecting the correctness of a thermostat's action by monitoring the supply air temperature, along with the ambient zone and setpoint.

FIG. 4 depicts a flowchart for detecting action correctness using a supply air sensor algorithm. In another embodiment, the correctness of a thermostat's action can be determined by monitoring the supply air temperature along with the ambient zone temperature and setpoint. A temperature sensor positioned in such a way as to read the supply air temperature can provide samples as an input to the algorithm. A monitoring algorithm can track changes in supply air temperature, zone setpoint and zone temperature. The zone temperature can be compared against the setpoint and evaluated for a change larger than some minimum offset.

If a change is not detected, the supply air temperature will be recorded as a neutral temperature. This is the temperature resulting from a neutral branch pressure—one that does not call for heating or cooling. In one method, a single neutral temperature can be recorded. In another method, the neutral temperature can be average over time to account for any erroneous readings. When a change is detected, the supply air temperature will be compared against the neutral supply temperature. If the zone temperature relative to the setpoint, and supply temperature relative to its neutral, have changed in the same direction, the zone can be registered as containing an incorrect-acting thermostat. Otherwise, the action is correct. Alternative methods can compare the supply temperature to a known neutral set by user or a value derived from the ambient temperature if no supply air is flowing. Further, the zone temperature trend can be monitored relative to itself rather than to the setpoint. Any approach or algorithm described above can execute continuously or periodically. They can be analyzed as samples are collected in real time or post-processed after multiple samples have been taken.

6.3 Detection of Proper Day/Night and Summer/Winter Operation

Based on main and branch pressures, as well as the zone temperature, the system may determine if day/night or summer/winter HVAC equipment is working properly. The following actions can be performed to evaluate for proper behavior: (1) monitor the main pressure to ensure change occurs as expected; (2) monitor thermostat to ensure proper behavior when day-to-night and night-to-day, or summer-to-winter and winter-to-summer change has been requested; and (3) proactive diagnostics such as changing the main pressure temporarily to verify the proper response from thermostats.

By continuously monitoring the main pressure, the characteristics of a day/night and a summer/winter system can be analyzed. The following is a subset of information which can be extracted by monitoring main pressure: time of day, day of year, and frequency at which the pressure changes. This can be used to ensure the system is properly changing at expected times. It can also be used to detect any erroneous or unexpected changes which can cause tenant discomfort. The main pressure value used in each mode, night and day or summer and winter, can be monitored to ensure the pressure applied adheres to the Day/Night or the Summer/Winter specifications.

A change in main pressure can be detected by analyzing subsequent samples for changes larger than some predefined threshold. In one method, this analysis can be performed on two subsequent samples at a time. Alternatively, a set of values greater than or equal to samples can be analyzed in a sliding-window fashion. Any type of well-defined filters can also be applied to properly condition the sample set for analysis.

Given the mode of the system (Night, Day, Summer or Winter) detected using the methods described above, day/night thermostats within the system can be analyzed for proper behavior. For systems that change action between modes, the action can be verified and compared against the appropriate behavior for the mode. The current action of each zone thermostat can be determined using methods described above. In addition to verifying thermostat behavior, the zone behavior can also be analyzed by monitoring the trend of the ambient temperature. Using methods described above, a positive or negative trend in ambient temperature can be determined. An error can be detected if the trend does not match the particular mode. One example of a detectible error is if the zone begins to cool after a transition from summer to winter.

For systems that change setpoint between modes, the setpoint can be verified directly if it is electronically communicated. Otherwise the setpoint can be deduced. After mode change, the branch pressure changes as a result of the setpoint change. Given the ambient temperature, neutral branch pressure, and throttle range, the following equations can be used to calculate setpoint. Note the following equations can only be used if the branch pressure has not saturated.

$$\text{SETPOINT (Direct Acting)} = \text{AMBIENT\_TEMP} + (\text{NEUTRAL\_PRESS} - \text{BRANCH\_PRESS}) * (1/\text{THROTTLE\_SLOPE (psi/f)}) \quad \text{(Eq. 7)}$$

$$\text{SETPOINT (Reverse Acting)} = \text{AMBIENT\_TEMP} + (\text{BRANCH\_PRESS} - \text{NEUTRAL\_PRESS}) * (1/\text{THROTTLE\_SLOPE (psi/f)}) \quad \text{(Eq. 8)}$$

Alternatively, the trend of the ambient temperature can be used to determine if the system is responding to a mode change.

To proactively determine if a day/night or summer/winter system is behaving properly, the main pressure can be temporarily changed while observing the branch pressure for proper response. The main pressure can be changed between modes. After each change the branch pressure can be monitored over time. Given the setpoint for a specific mode, thermostat throttle range (or more specifically, throttle slope), and ambient temperature, the expected branch pressure can be calculated and compared against the actual branch pressure. The system can conclude an error is present if the difference between the actual and expected branch pressure is greater than some error tolerance percentage. The following equations can be used to calculate branch pressure.

BRANCH_PRESS (Direct Acting)=AMBIENT_TEMP+(BRANCH_PRESS−NEUTRAL_PRESS)/THROTTLE_SLOPE (psi/f)     (Eq. 9)

BRANCH_PRESS (Reverse Acting)=AMBIENT_TEMP+(NEUTRAL_PRESS−BRANCH_PRESS)/THROTTLE_SLOPE (psi/f)     (Eq. 10)

Alternatively, the setpoint given the branch pressure can be verified using Equations 7 and 8.

6.4 Detection of Stuck Actuator, Damper or Valve

Temperature overshooting or non-responsiveness can be symptoms of a malfunctioning valve, damper or vent. By monitoring the branch pressure and zone temperature, a prediction can be made as to the state of error. Diagnostic control signals can be sent to the suspect zone during an unoccupied state to validate the failure cause. If the zone continues to overshoot its setpoint, then the vent is stuck open. If the zone is non-responsive to setpoint changes, then the vent is stuck closed.

Figure 5:
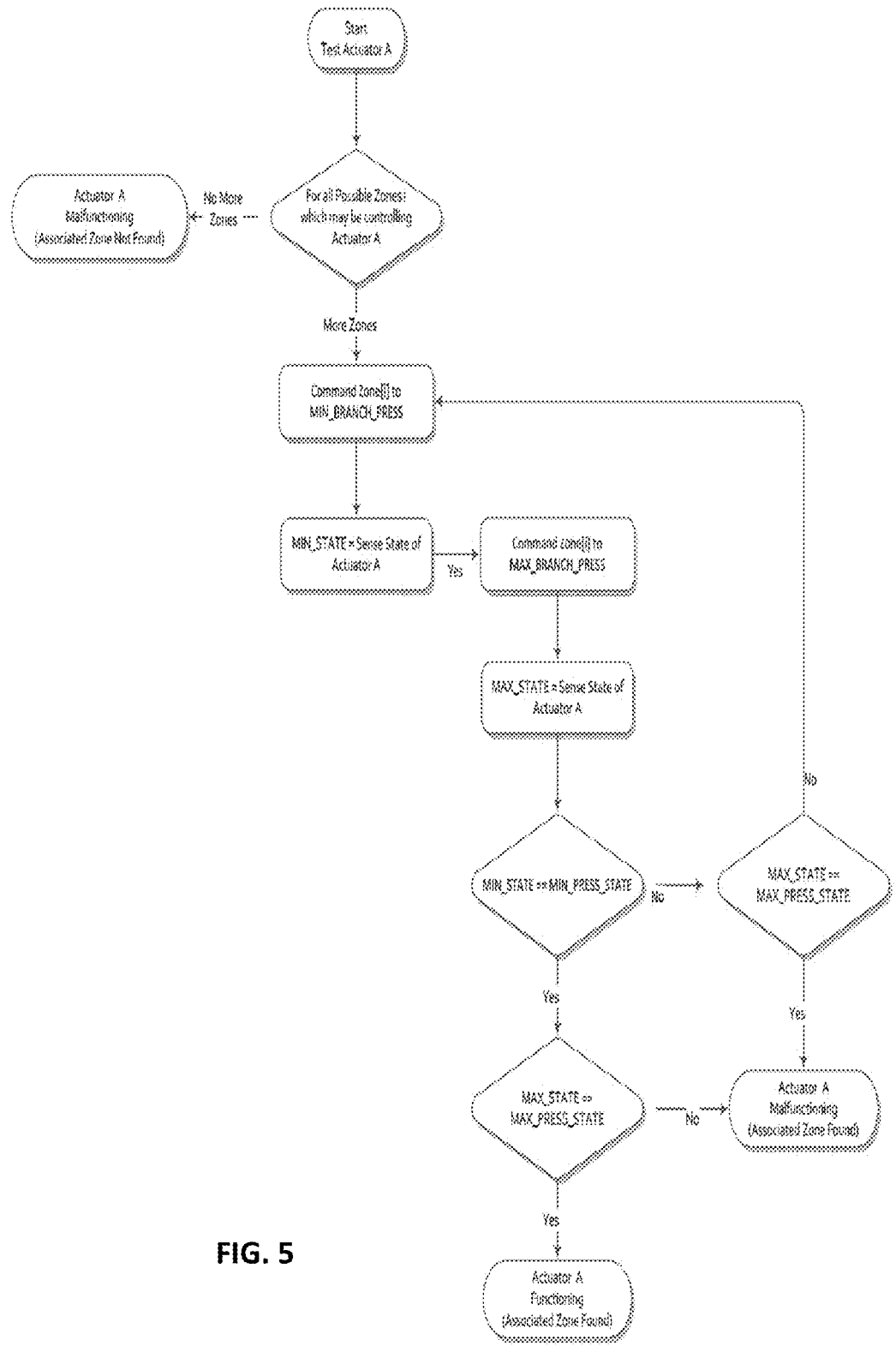
FIG. 5 illustrates a flowchart for a method of detecting a malfunctioning valve/vent by using information from distributed sensors.

Another feature of the disclosed system is the detection of malfunctioning actuators using distributed sensors. FIG. 5 depicts a method of diagnosing a malfunctioning valve/vent using information from distributed sensors. The distributed sensors can be made up of thermostats with built-in sensors, or standalone sensors, or both. Sensors can be positioned such that the output or state of a valve, damper, or vent can be directly measured. Any characteristic which reflects an actuator's position can be sensed, including, for example, temperature, air flow, mechanical displacement, etc.

Commanding the zone branch to a minimum or maximum specified pressure and analyzing the resulting state of the actuator can indicate whether or not the actuation is functioning properly as defined in the flowchart. Proper delays (not depicted) can be strategically embedded into the flowchart to ensure stabilization of pressures, temperatures and other variables.

In one embodiment, the associations between zones and actuators are known. In another, they can be deduced by trial and error, as shown in the flowchart. In case they are not known ahead of time, the relationships can be recorded once derived using the algorithm presented here. Subsequent actuator analysis routines can leverage the known relationships derived here.

Figure 6:
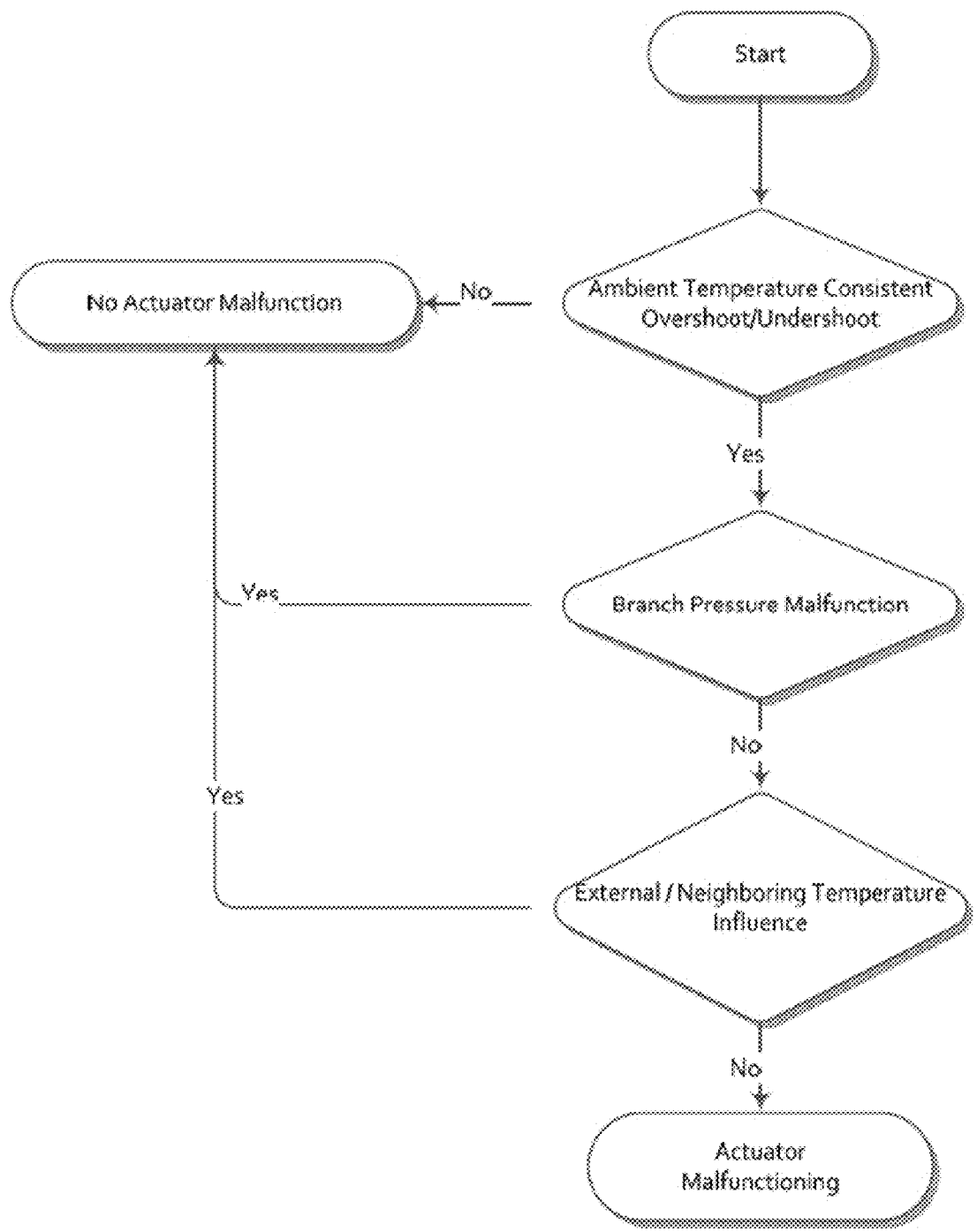
FIG. 6 illustrates a flowchart for detecting the malfunctioning of actuators over time.
Figure 7:
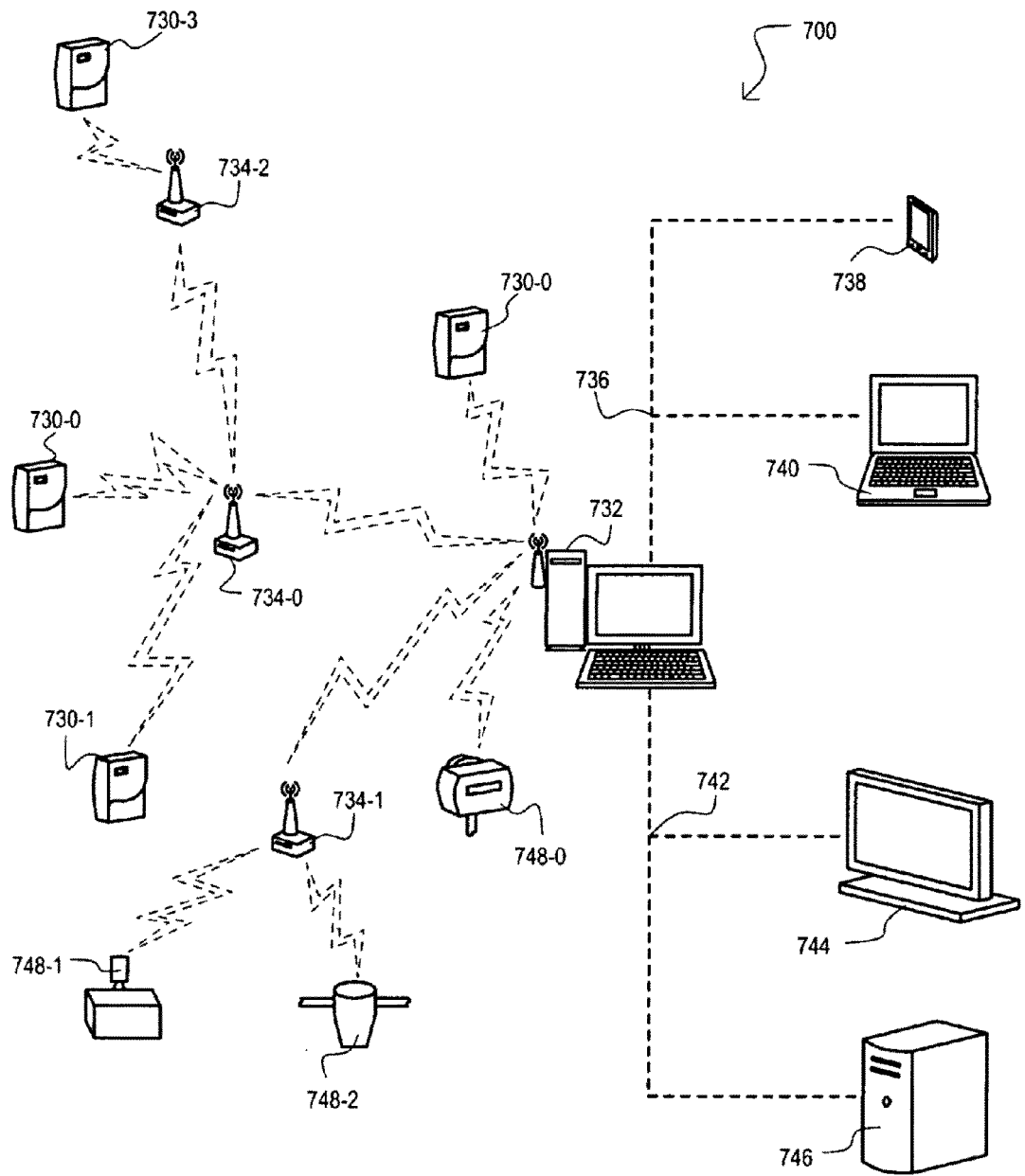
FIG. 7 is a diagram showing systems and system components according to various embodiments.

In another method, a malfunctioning valve/vent can be diagnosed by using information from a set of thermostats in proximity to the actuator in question. FIG. 6 depicts a flowchart which illustrates this method. By analyzing the zone temperature response to branch pressure over time, a conclusion can be derived on the state of the actuator. If the ambient temperature of a zone repeatedly overshoots or undershoots the setpoint, the zone should be analyzed. One way to detect such a zone would be to integrate the difference between ambient temperature and setpoint over time. The resulting "area under the curve" can be compared to an error tolerance threshold to determine whether or not the zone is malfunctioning in some way. Another way to detect an error is to compute a moving average of the difference between ambient temperature and setpoint. When the average reaches a specific threshold, an error can be flagged.

The branch pressure can be analyzed during the times of ambient temperature errors. Using methods described herein, it can be verified that the branch pressure is properly tracking ambient temperature. If the branch pressure is not tracking temperature, the thermostat can be a cause of the temperature errors and a malfunctioning actuator cannot be reliably identified. If the branch pressure is tracking temperature, then the thermostat is properly calling for heating or cooling and the thermostat can be eliminated as a potential cause.

Temperature influence from exterior temperatures as well as neighboring zones can be eliminated to isolate the cause of the error. One way to detect such influence is to measure the temperature gradient or difference between the zone in question and a particular neighboring zone. If the gradient is large, the neighboring (or exterior) temperature can influence the zone. See Section 6.12 below. By tracking the magnitude and frequency of occurrence, an influence can be determined. If the consistent overshoot of ambient temperature cannot be attributed to exterior or neighboring zones, the zone actuator can be identified as the cause.

6.5 Detection of Throttle Slope

The system also is capable of Detection of Throttle Slope. Based on the branch pressure response to a given temperature increase, the thermostat's throttle slope setting can be calculated. This can be monitored over time naturally, or the system can command a step response (setpoint change) to observe the effective throttle range. Throttle Slope is completely independent of the connected actuator's spring rate (spring range).

By analyzing other aspects of an HVAC system the throttle slope can also be detected. Electro-pneumatic thermostats could change the throttle slope adjustment based on the zone's step response. A step response would be accomplished by driving the thermostat into full heat or cool and measuring the temperature and branch pressure response over time. A change in the step response could signal problems with the HVAC mechanics such as leaky pneumatic lines, stuck dampers, or faulty actuators, as well as other problems with the fan unit.

Conventional stats can alert maintenance if the throttle slope is out of specification tolerance. Proper adjustment will increase the response time while decreasing temperature overshoot and oscillations. Calibration errors can be compensated for if the throttle slope changes or is out of specification tolerance.

One method to detect the throttle slope of a thermostat is to command a setpoint change and monitor the step response of the branch pressure. The commanded setpoint must be properly sent to prevent the branch pressure from saturating. A new setpoint command can be issued to a particular thermostat. A trial and error approach can be taken to find the correct setpoint which does not saturate the branch pressure. One method for accomplishing this would be to use a binary search. Each iteration through the search would apply the new setpoint to check for saturation. The branch pressure response is monitored and applied to the following equation to generate the Throttle Range.

THROTTLE_SLOPE (psi/° F.)=|BRANCH_PRESS−NEUTRAL_PRESS|/|AMBIENT_TEMP−SETPOINT|     (Eq. 11)

An alternative throttle slope detection method would be to passively analyze samples from the zone. Rather than commanding a setpoint change, normally scheduled setpoint changes can be used following the same method above. Natural drifts between zone temperature and the setpoint can also be used by applying the same inputs to Equation 11 above.

6.6 Detection of Throttle Range

The actuator's range of motion is referred to as the spring rate or spring range. The throttle range is the temperature delta which would cause the actuator to go from full open to full closed. The throttle range combines throttle slope with spring range, and is therefore dependent on the specific actuator used with the thermostat.

For example, for an actuator with a spring range of 3-8 psi (full closed to full open), a thermostat that outputs 3 psi at one ambient temperature, and 8 psi at a temperature 5 degrees higher or lower than that original temperature, would have a throttle range of 5 degrees. It would have a throttle slope of 5° F./(8-3 psi)=1° F. per psi (or 1 psi per degree F.).

It is desirable to know the spring rate and/or throttle range for each zone in order to adjust WPT calibration or responsiveness appropriately to ensure occupant comfort and optimized energy consumption. It is currently difficult to determine these parameters without manual inspection of each actuator. Also, the actuator's or thermostat's behavior may change over time, so it is impractical to repeat a manual evaluation periodically. This section describes automated methods to determine these system parameters.

Throttle range may be detected in several ways. One method to detect the throttle range uses a set of distributed sensors as described in Section 6.4. To determine the throttle range of a particular zone, the zone thermostat can be commanded to "search" for the two edges of the throttle range. This search can be performed during unoccupied hours to minimize tenant discomfort. The edges being detected are the minimum and maximum pressures (MIN_PRESS and MAX_PRESS) at which an actuator is fully open or fully closed. The throttle range can be calculated using these values as shown in Equation 13.

The search algorithm will cause the zone branch pressure to iterate through several values while the actuator output is monitored. The actuator output is monitored as described in Section 6.4. Any type of well know search algorithm can be used, including a simple linear search where the pressure is commanded to start at zero and increase to the main pressure, or a binary search. The search can also start off by making coarse adjustments followed by finer adjustments as it narrows in on an edge. The association between thermostat and actuator is either known or can be detected using this algorithm in the same manner as described in Section 6.4. At each iteration, the algorithm will determine the first sign of the actuator opening or closing. For example, if the airflow between the previous and current iteration changes from zero by some positive amount, an edge is detected. Alternatively, if the airflow changes from some positive amount to zero, another edge is detected. This process using the algorithm can be repeated in any pattern to further ensure the correct edge is detected. Repeating the process will also ensure changes in throttle range are tracked and reported in case of abnormalities. Once both edges are found, the throttle range can be calculated using Equation 13.

Another method to detect the throttle range is by analyzing the air flow of a particular zone's branch line. A similar search process using an algorithm can be performed as described above. Rather than looking for the actuator output using a sensor, the air flow can be monitored. Another method to detect the throttle range is by analyzing the zone characteristics including branch pressure, ambient temperature, neighboring zones, and exterior temperature. This can be performed in real time as the zone operates normally or is manually commanded. In manual mode, the search can execute until completion or iterate through several values over time, for example, one iteration per day during unoccupied hours. At different branch pressure iterations, the ambient temperature can be monitored over time using the methods described above. The process of using the algorithm can eliminate any influence from neighboring zones or exterior temperatures to isolate changes to those caused by the local actuator. If no change in ambient temperature is detected over time, the actuator can be considered closed. If a small change in ambient temperature is detected over time, the actuator can be considered open. The algorithm will search for the edge in a similar manner as described above using the ambient temperature change.

$$\text{THROTTLE\_RANGE} = \text{TEMP\_MAX\_RANGE} - \text{TEMP\_MIN\_RANGE} \quad \text{(Eq. 12)}$$

$$\text{THROTTLE\_RANGE} = (\text{MAX\_PRESS} - \text{MIN\_PRESS})/\text{THROTTLE\_SLOPE (psi/° F.)} \quad \text{(Eq. 13)}$$

6.7 Detection of Leaking Main or Pneumatic Line

It is important to detect and repair leaks in the pneumatic system since they can cause occupant comfort issues, increase energy consumption, cause annoying audible noise, and overburden the air compressor, etc. The system uses one or more of several possible sensors, including pressure sensors, airflow sensors, and audible sensors.

Main pressure sensors may be included on some or all WPTs in the system, or added separately. By tracking the main pressure supply in a distributed sensor network over time, the controller can analyze the readings for possible indications of leaks. If the controller notices a drop of greater than 10% (for example) in the main pressure from one or more sensors, it indicates a possible leak either on the main side or possibly a significant leak on a branch side. If the main pressure on multiple WPTs drops approximately the same amount, then the controller issues a warning that the fault might be with the main regulator, or that the leak may be close to the compressor. If the main pressure variations throughout the system are different, then the controller issues a warning indicating a localized leak farther from the compressor. The system can narrow down the location by identifying the WPT with a main pressure sensor reading the lowest pressure.

If one or more airflow sensors are added to the system at various locations, the controller would monitor the standard airflow throughout normal operation. The controller would record the normal maximum and minimum flow rates over the course of several days or perhaps several seasons. Once the baseline is established, the system controller would select a threshold of 10% (for example) higher than the max flow rate from the baseline data. If this threshold was ever exceeded, the controller would issue a warning. The controller could identify which airflow sensor was reading above the threshold to localize the leak.

The controller uses branch pressure sensors to collect and analyze data to detect pneumatic system leaks. This avoids the need to also add main pressure sensors. The controller performs a similar baseline operation as it would for airflow sensors or main pressure sensors. It collects historical data over time and under various conditions. If the controller notices a sudden change (based on processing historical data points) in the calibration offset for a single zone, and that offset was in the direction of a reduced branch pressure, then the controller flags that zone for a possible main or branch leak affecting that WPT. The controller also checks neighboring zones to determine if their calibration offsets have also suddenly changed, or if they have remained stable during the same time period. If one or more of them have also changed, then the controller issues a warning that there may be a main leak, since multiple WPTs are affected. If the neighboring zones have not changed, then the controller issues a warning that there may be a branch leak only on the single zone.

The system may conduct a cooperative pressure test for active leak characterization. This would allow for off-hour system pressure testing where all the thermostats are temporarily set to max branch pressure (low setpoint for direct acting, high setpoint for reverse acting). This will make the branch pressure and main pressure roughly equal, eliminating the need for a dedicated/separate main pressure sensor in each WPT in addition to the existing branch pressure sensor. During this test, if the controller detects any low branch pressures (for example, less than 18 psi in a 20 psi system), then the controller would issue a warning for each of the low pressure zones. The controller would also identify the WPT with the lowest branch pressure to help localize the probably area of the leak. After this test is complete, the controller would command all of the WPTs back to their normal setpoints.

6.8 Detection of Faulty Compressor or Main Regulator

The main regulator controls the main line pressure typically to 20 psi for conventional 1-pipe or 2-pipe systems. There can also be dual regulators set to different pressures for Day/Night or Summer/Winter systems. A pneumatic relay selects between the two regulators depending on the system operating mode. A fault in any of the main pressure regulators can cause damage to the pneumatic thermostats or actuators, or can affect their performance by altering their calibration or providing insufficient pressure to drive the actuators. It is desirable to detect any deviation from the expected main pressure to avoid damaged equipment, uncomfortable occupants, or wasted energy.

The central controller monitors WPT branch pressure sensors and WPT main pressure sensors (if available) periodically over time. The system can be used to detect an over-pressure fault. If the central controller or local WPTs detect a main or branch pressure reading greater than [Main_Regulator_Setting (psi)+Error_Tolerance], an over-pressure fault may be suspected. The controller may then issue a warning that the main regulator is faulty.

Historical branch pressure maximums would always be less than or equal to main pressure in a properly operating system, so even without dedicated main pressure sensors, WPTs can still detect a faulty condition if the branch pressure ever rises above the expected main level. Such an event would indicate that the regulator is faulty and over pressurizing the system.

The system can be used to detect an under-pressure fault. If the central controller or local WPTs detect a main pressure less than [Main_Regulator_Setting (psi)−Error_Tolerance], a under-pressure fault may be suspected. The controller may then issue a warning that the main pressure is low, and that there is likely either an air leak or a faulty main regulator, or the compressor cannot keep up with the air demand.

In a dual regulator system, the controller may perform the same steps described above for each of the regulators, and a deviation from the expected pressures could indicate a faulty regulator, a faulty compressor, a faulty pneumatic relay or an air leak.

Main pressure statistics could be used over time to determine system health. Several of the same algorithms discussed in Section 6.7 can be used to also warn that the main regulator or compressor may be faulty. Lower than expected pressure readings could indicate either a leak or faulty compressor or regulator.

The system can be used to diagnose compressor cycling. The controller monitors the WPT main pressure sensors over time. Most main pressure regulators will have a slight output fluctuation corresponding to the compressor recharge cycles. The pressure increases slightly while the compressor is charging, and the pressure decreases slightly as the pressure in the compressor's ballast tank is discharging. The controller monitors these slight changes in pressure that correspond to the compressor recharge cycles, and computes the average duty cycle of these recharge cycles under various conditions. When the controller notices a significant change in the period of the recharge cycles, then it issues an alert that the compressor may be malfunctioning or there is a downstream air leak. If the cycling stops completely, then the controller issues an alert that the compressor is completely offline (seized, lost power, major leak).

A dedicated pressure sensor may be added directly before and after the main regulator. The controller could monitor these two sensors to more easily isolate faults. If the regulator was faulty then the downstream pressure sensor read an unusually high or low value. If the compressor was faulty, then the upstream pressure sensor read an unusually high or low value, but the downstream sensor read a normal value or at least the same value as the upstream sensor (if the compressor output pressure dropped below the regulator's pressure setting). The cycling period of the air compressor (discussed earlier) can be much more easily observed with this sensor placed before the main pressure regulator, since the pressure swings will be much more dramatic.

6.9 Compensation for Low or High Pneumatic Pressure

As discussed in earlier sections, there are a variety of conditions that may cause a lower than expected pneumatic air pressure (air leaks, faulty compressor, faulty main regulator, etc.). The primary reason for higher than expected pneumatic pressure is a faulty main pressure regulator.

The branch pressure of some thermostats is directly affected by a change in main pressure. A direct-acting thermostat's operation is proportional to the main pressure change. A reverse-acting thermostat's operation is inversely proportional to a main pressure change. For these types of thermostats, the central controller of the local WPT would monitor the change in main pressure, and would apply a compensation factor to the setpoint command (or direct branch pressure output) in order to output a correct branch pressure to the actuator. In case of a system-wide pressure change (compressor or main regulator fault), it is likely preferable for the central controller to send out commands to all of the WPTs to be sure that all of them are aware of the system-wide failure and the compensation adjustment.

Similarly, the local WPT could perform an ongoing auto-calibration process to make sure that the branch pressure that it was outputting always matched the theoretical branch pressure based on its other system parameters. See Equations 1 and 2. This would allow the WPT to adapt to certain failures, as long as the main pressure never dropped below the desired branch pressure.

If the fault is caused by an air leak, or any other reason such that the main compressor has trouble keeping the pressure at its normal point (20 psi), then the system controller can take actions to minimize the impact of this fault until it is fixed. The controller sends out setpoint change commands to each WPT at staggered intervals instead of together at the scheduled time. This avoids having multiple attempts to charge up the pressure in the branch lines at the same time, over-burdening the compressor.

The controller can send out setpoint change commands to certain low-priority zones which would cause them to consume less air, so that the high-priority zones have extra air available for normal operation. Some thermostats consume less air when they are set to a high or low branch pressure. For electro-pneumatic thermostats (where the electronics directly control the branch pressure or airflow), it is easy to completely shut off all air consumption by closing the regulating valve fully.

6.10 Detection and Compensation of Audible Pneumatic Noise

Audible noises generated from pneumatic thermostats are common and some noises may be loud enough to annoy occupants when they occur. Some of these noises include intermittent venting noise when the branch line has to decrease in pressure, constant venting noise from the valve orifice during normal pressure regulation, intermittent charging noise when the branch line has to increase in pressure, humming noise when the thermostat valve causes an oscillation, or hissing noise when a seal or diaphragm is damaged or when contaminants are present in the thermostat's valve.

The humming or hissing noises as well as the venting noise can be particularly annoying since they may be constant under certain conditions. The other noises are generally intermittent, so they may be more tolerable if they are not too loud. It is desirable to detect the presence of audible noise, so that the WPT can either compensate for it or alert maintenance personnel to repair the issue prior to annoying the occupant.

The WPT can contain a simple audio transducer. This transducer would be monitored by the WPT's internal microcontroller either constantly or periodically (to preserve battery life) in order to detect audible noise above a selected threshold using common audio level detection techniques. The WPT can alternatively use its main and/or branch pressure transducers to detect pressure oscillations in the audible frequency range. It is likely that whatever is causing the audible noise may impart pressure oscillations in the main or branch lines. The WPT would check for an audio frequency (likely in the 20-10000 Hz range, due to mechanics of the thermostat) oscillation in the pressure transducer output signal using common audio level detection techniques.

The system can be used to differentiate audible pneumatic noise from other environmental noise. If an audio transducer is used, then the WPT must determine if the transducer is detecting pneumatic noises or simply other noises in the environment (humans talking, machine noises, etc.) The WPT's microcontroller can perform basic signal analysis to determine if signals detected from its audio transducer are due to human or machine noise in the environment or due to a failure in the pneumatic system.

Using one method, the WPT looks for constant noise level and frequency over a period of several seconds. Humans talking or most other environmental noises will not be constant amplitude and frequency.

Using another method, the WPT can look for specific frequency ranges that are known to be generated by pneumatic venting, charging, humming, or hissing. The system can use an analog bandpass filter and an associated level detector for each of the desired frequency ranges or can perform digital processing such as a fast Fourier transform (FFT) to check for energy in the target frequency ranges.

In another method, the system can use multiple microphones constructing microphone arrays. The WPT may contain audio transducers both internal and external to the WPT enclosure. It compares the signal levels between the two transducers to determine if the sound is originating internally or externally. A higher amplitude on the internal transducer than the external transducer indicates the source is internal and is likely due to a pneumatic issue, rather than a noise source in the room.

Using another method, a single noise-cancelling microphone may be used if mounted on one of the sides of the WPT enclosure. Since the WPT is vented, noises within the room will generally have equal levels on both sides of the noise-cancelling microphone and will therefore be cancelled. But noise generated from inside the WPT will have a much higher amplitude on the inside microphone port than the outside, so it will not be cancelled and will be detected as pneumatic noise.

In another method, the WPT can use input from an occupancy sensor and/or a real-time-clock to determine if it is likely that a detected noise came from the environment instead of the WPT's pneumatics. If no occupancy is detected, or if it is late at night or on a weekend, then it is less likely that the noise came from the environment.

In another method, the system can detect noise using neighboring zones. When a WPT detects a possible noise, it can wirelessly communicate with WPTs in its neighboring zones (either directly or through a central hub) to see if they also detected noise at the same time. If one or more neighboring zones also detected noise in the same time span, then it is very likely that the noise is from the environment.

It is useful for the WPT to differentiate the normal operating noises of the thermostat from the abnormal noises. It can still try to compensate for either, but the abnormal noises could also raise an alarm condition.

When the WPT changes the setpoint, it knows that the branch line will either charge or vent for several seconds to respond to the setpoint change, so any increase in noise detected during that time frame can be attributed to the setpoint change action.

Similarly, the WPT can monitor the branch pressure, and if it detects a significant change over a period of time (due to ambient temperature changes), then it can expect to hear some intermittent venting or charging noise.

The system can be used to compensate for intermittent noises. The WPT can take certain actions to minimize intermittent noises that are caused by normal operation of the system. When a setpoint change command is received, the WPT may determine if the branch line will need to be vented or charged. Venting is typically much louder than charging, so there is more of a need to compensate for venting noise generation.

$$\text{IF New\_Setpoint} > \text{Old\_Setpoint AND} \\ \text{WPT\_Type} == \text{Direct\_Acting\_Stat, Then Venting.} \quad (\text{Eq. 14})$$

$$\text{IF New\_Setpoint} < \text{Old\_Setpoint AND} \\ \text{WPT\_Type} == \text{Reverse\_Acting\_Stat, Then Venting.} \quad (\text{Eq. 15})$$

Once the WPT determines that the branch line will need to be vented (reduced branch pressure), and if it already determined that this particular WPT has a loud venting noise (exceeds a specified audio detection amplitude), then the WPT can decide to slow down the normal venting speed to decrease the venting noise amplitude.

In a conventional thermostat system, the WPT can change the setpoint control by a fraction of a degree every second instead of making the full adjustment immediately. In an electro-pneumatic system, the WPT can open the proportional vent valve less than its normal venting orifice size to slow the venting airflow. The WPT can additionally use knowledge about the volume of the actuator to determine if slowing the venting will have an adverse affect on the performance of the zone. If the actuator is small (has a small pneumatic volume), then slowing the venting will have a minimal effect on zone performance. If the actuator is large, then the WPT may need to include that in its decision logic so that it doesn't cause sluggish temperature control behavior. The WPT can use select parameters (zone temperature, new setpoint temperature, occupancy detector) to determine if it is a high priority to change the pressure quickly or if it can be vented slowly in a specific instance. For example, if the zone temperature is currently outside of a designated comfort zone (such as 68-76° F.) and occupancy is detected, and the new commanded setpoint temperature is inside the comfort zone, then the WPT should consider it a high priority to adjust the pressure quickly to ensure optimum temperature control response for the zone. However, if the reverse is true (setpoint changing from inside the comfort zone to outside the comfort zone), then there shouldn't be a high priority to vent quickly and potentially annoy any occupants.

The system can also be used to compensate for constant noises. In cases of humming and some cases of hissing, it is common that these noises only occur under specific conditions. When the WPT detects the presence of a constant noise, it can attempt to make minor control action adjustments to eliminate the noise. The WPT may temporarily adjust the setpoint control temperature up or down a fraction of a degree to see if that is enough of a change to eliminate the oscillation causing the noise. The WPT may temporarily swing the setpoint control temperature up or down by several degrees, and then immediately return to the correct setpoint control position. This action may also cause slight mechanical variations to prevent the oscillation from continuing or restarting.

If the WPT determines that a noise is dependent on a certain branch pressure or venting/charging airflow rate, then the WPT can attempt to avoid the action that caused the noise. In particular, if the noise is flow rate dependent, then the WPT can try to avoid the specific range of flow rates that cause the noise, and may still be able to control the temperature of the space effectively. This is particularly true for a two-pipe system, where normally the only tradeoff for adjusting the flow rate would be actuator response time. For a one-pipe system, it may be more difficult to avoid certain flow rates, but as long as the range of flow rates is not too wide where noise is present, then the thermostat can try to skip over that range of pressure (flow rates), which should only cause minor temperature comfort tradeoffs. If the WPT's attempts to compensate for constant noises fail, then the WPT can generate a system error/alarm notification for service.

6.11 Mechanical Wear Analysis

Currently, it is difficult to predict when a mechanical component in a pneumatic HVAC system may be worn out and require replacement. Existing pneumatic HVAC systems have no method for monitoring most system parameters such as zone temperatures, branch pressures, setpoint activity, actuation cycles for dampers, actuation cycles for water valve actuators, actuation cycles for pneumatic valves, cycles for diaphragms and seals, etc. It would be ideal to have a method to measure or accurately estimate the amount of wear-and-tear that a component has experienced over time so that maintenance can be performed prior to component failure. This section discloses a method to predict equipment wear, so that the system can proactively recommend service or end of life for components.

One method is by monitoring the amplitude of branch pressure fluctuations over time, which directly corresponds to the number and amplitude of damper or valve actuation cycles and/or the number and amplitude of pressure cycles affecting diaphragms, seals, tubing, and filters. Another method is for the system to correlate known equipment failures with other equipment in the system that has experienced a similar amount of use.

The system can be used to predict failure based on usage (wear and tear). The WPT controller or central controller monitors the branch pressure at predetermined intervals. The controller maintains a sum of the magnitude of change in branch pressure at each interval, which represents the amount of stress the pressurized and moving components experience.

Total_Branch_Changes=Prior_Total_Branch_Changes+AbsoluteValue(Current_Branch_Pressure−Prior_Interval_Branch_Pressure)  (Eq. 16)

Since HVAC actuators have a narrower operating range (typically 3-8 psi or similar) than the entire branch pressure control span (which is typically 0-20 psi), the estimation of the amount of actual actuator movement can be further refined, instead of also including overall pneumatic stress of the tubing, seals, diaphragms, etc. For an actuator with a pressure response range of 3-8 psi (full closed to full open for example), a total cycle from closed to open and back to closed is 10 psi. The system only needs to only account for pressure changes between 3-8 psi, since that is the only range that causes actuator movement.

If (Prior_Interval_Branch_Pressure>8); then PBP=8  (Eq. 17)

If (Prior_Interval_Branch_Pressure<3); then PBP=3  (Eq. 18)

If (Current_Branch_Pressure>8); then CBP=8  (Eq. 19)

If (Current_Branch_Pressure<3); then CBP=3  (Eq. 20)

The next step would be to calculate the running total of pressure changes within the 3-8 psi window.

Total_Actuator_Pressure_Changes=Prior_Total_Actuator_Changes+AbsoluteValue(PBP−CBP)  (Eq. 21)

The next step is to calculate the equivalent number of complete actuator movement cycles (closed to open back to closed).

Total_Actuator_Movement_Cycles=Total_Actuator_Pressure_Changes/((8−3)*2)  (Eq. 22)

Either one of these sums are compared against a threshold that indicates the amount of pressure or mechanical cycling experienced by the mechanical components. A damper actuator manufacturer may claim an expected life of 10 years for the device if it is cycled from closed to open and back to closed five complete times per day. Thus the total wear-life threshold would be 5*365.24*10=18,262 complete cycles. The next step is to detect if the actuator in the monitored zone is within, say, 80% or more of its expected wear life. If Total_Actuator_Movement_Cycles>(80%*18,262), then the controller sends a maintenance warning to inspect or replace the actuator. When maintenance personnel replace or service a component, they can reset or reduce the wear counter on the monitoring system as appropriate.

The system can be used to predict failure based on failure of other devices. When a component fails in the HVAC system, the maintenance person can enter that information into the main control and monitoring system. It will be able to provide alerts such as "Damper Actuator in Zone #1234 Failed on Feb. 5, 2013."

The monitoring system can use that baseline information to determine if other similar components are at risk of failure. It does this by comparing the wear-and-tear evaluation described for the known failed component against the same measurement for other system components. If other components have at least, say, 80% as much wear-and-tear as the failed component did at the time that it failed, then the system can alert maintenance to address those components prior to failure. This is particularly useful if some components start to fail prior to their manufacturer's claimed lifetimes.

If the system determines that a particular part needs to be replaced, the system may be connected to the Internet to suggest appropriate repair parts needed and where to obtain them. They system could also automatically order the parts and have them delivered to the facility manager.

The system could also recommend service providers to perform repair/replacement based on system performance issues. Based on the diagnosis, the system could suggest appropriate local vendors that could perform the suggested service, and send a parts lists to that vendor so that the repair technician arrives ready to repair the problem promptly.

6.12 Automatic HVAC System Characteristic and Energy Optimization

At "select times" the HVAC system controller can perform specific control and monitoring actions to gain further knowledge about the particular HVAC mechanics and each of the zones that may not be possible by simply passively monitoring system data over time. The "select times" can be when user impact would be minimized, such as the middle of the night, or on weekends. This can also be done as part of the commissioning process (immediately after installation or repair) to validate and tune system operation.

The HVAC controller can command one WPT to maximum heat and monitor all relevant sensors. For example, assuming the current setpoint and zone ambient temperature are both 72° F., the HVAC controller may send a setpoint change command (such as 85° F.) to the target WPT. The HVAC controller monitors branch pressure sensor data from that WPT every second over the next five minutes. The HVAC controller monitors zone temperature readings from that WPT every minute over the next 1-3 hours. The HVAC controller sends a setpoint change command (back to normal) to the target WPT to conclude the test. The HVAC controller then analyzes the data.

The system can be used to test branch pressure response. If the branch pressure took a long time to reach 0 or 20 psi (depending on direct- or reverse-acting thermostat) immediately after the setpoint change command, then the HVAC controller knows that the actuator for that zone has a large air volume, or that the flow is somehow restricted to that actuator. If the branch pressure took a short time to reach 0 or 20 psi, then the controller knows that the actuator has a small air volume. The controller can use this information in the future to adjust the parameters of its feedback control loop. For example, it may increase the control loop gain in the case of slow branch pressure response to compensate for sluggish temperature control response. Conversely, it may decrease the control loop gain in the case of fast response to avoid oscillations and energy inefficiency.

The system can be used to test zone temperature response. If the zone temperature only increased from 72° F. to 75° F. during the duration of the 1-3 hour test, then the HVAC controller knows that: (1) the zone may be underpowered for heating; (2) the zone may be very large; or (3) the zone may be affected by conditions in neighboring zones.

If the zone temperature increased from 72° F. to 85° F. during the duration of the test, then the HVAC controller knows that: (1) the zone may be small; or (2) the zone may be overpowered for heating.

The system may be used to test neighboring zone influence. The control system drives the setpoint (branch pressure) of one zone to heat or cool and measures the response of a passive neighboring zone to understand the building dynamics. If the system detects only a small temperature change in a neighboring zone due to the setpoint change in the other zone, it can use this information to largely ignore neighboring zone infighting issues. If the system instead detects a large temperature change in the neighboring zone, then it can modify its control logic to have those two zones cooperate in the future. When one zone's setpoint is changed, it can ensure that the neighboring zone is set to a similar setpoint automatically to avoid wasting energy by having the zones fight (one heats while the other one cools). Or, maximum and minimum relative zone setpoints can be enforced to ensure two zones do not fight. For example, zones A and B are adjacent and have setpoint limits of 65-75° F., but since they have an influence on one another, zone-B limits can dynamically be set to zone-A±5° F.

Based on branch pressures from neighboring zones, predictions can be made regarding the strength of each zone (high, medium, low) and their influences on each other. Predictive heating and cooling patterns can be used to ensure neighboring zones are not fighting.

The system may be used to prepare heat-load maps for energy efficiency diagnostics. Heat-load maps can be generated using location data as well as the average branch pressure value (or pressure delta from the neutral control pressure). Branch pressure is monitored and averaged over eight hours of occupied time for each WPT. These values are plotted on a map of the building zones corresponding to each thermostat. Zones that have an average branch pressure farther from the neutral point (typically 8 psi) than other zones indicate that they are calling for more heating or cooling on average than other zones. This information can guide maintenance people to verify proper insulation and mechanical operation of those zones.

The system can also be used for building insulation characterization. In addition to the heat-load map, another method to characterize the building insulation is described here. The system could be used to quickly identify problem areas in the building for energy inefficiency.

Building insulation efficiency can be measured at night when the HVAC system is powered off and the outside air temperature is significantly higher or lower than room temperature. Temperature measurements can be wirelessly collected from all thermostats periodically, starting from the time that the HVAC system is turned off for the night. Thermostats with the lowest ambient temperature change between the first and last temperature readings after several hours of HVAC inactivity indicate better insulated zones. Conversely, zones with the highest ambient temperature change during this test indicate poorly insulated zones.

This system can recommend energy-saving suggestions based on overall system performance. What-if analysis and perturbation (sensitivity) analysis can be used on various pneumatic parameters for energy-saving scenarios. The system could also recommend ways to reduce energy consumption. The system is capable of calculating estimated energy usage. By measuring how far off the neutral point each branch pressure is reporting, an overall energy estimate can be assessed (using knowledge of the outside temperature). For example, zones that have met their setpoint would report 0% energy average. Zones that are calling for full heating or cooling would report 100% energy average. This parameter can be used to tune the building to run at a more efficient setting. Theory states that if all zones are reporting 0%, there may be too much energy being used to satisfy the zones. Likewise, if all zones were reporting 85%, then the tenants' comfort may be in jeopardy. Targeting an energy state of 20-30% could give the best balance between comfort and efficiency.

In addition to energy savings, branch pressure analysis can be used to calculate total energy consumption. By accumulating the divergence of the branch pressure from its neutral point over time, the total amount of heating or cooling energy used for a particular zone could be estimated. The system can also be used for energy performance monitoring. For example, the system can perform a cost and fault correlation. The system will formulate the relationship between the energy cost and various pneumatic system fault patterns. The cost per off-pressure, off-degree in temperature, or off-hour schedule will be analyzed per building/zone/thermostat.

6.13 Schedule Monitoring

The system can be used to help to determine schedule anomalies, including zones inadvertently left off a schedule. Location information (from manual entry, wireless triangulation, wireless proximity, GPS, etc.) can be used to identify zones within the same region that may be on competing schedules. The wireless proximity method can incorporate radio frequency receive signal strength indicator (RSSI) thermostats as part of the system in known locations to provide a rough location map to help diagnose zone behavior (exterior/interior room) or zone interactions. Zones with start/stop times that do not corresponded to zone occupancies, and the temperature behavior of a zone that does not follow the scheduled setpoint could signal mechanical failures or communication problems.

Based on schedules, an easy-to-read pie chart can be used to display average occupied hours per zone. This can be reported for weekdays as well as weekends. Schedules can be used to: (1) report total occupied hours per day; or (2) report percentage occupied hours in the month.

Schedule override or manual setpoint change events can track a tenant discomfort metric. Setpoint change frequency can be used as a global check for all equipment controlling the system. For example, a building management system could be unintentionally sending setpoint change requests canceling out a user's manual setpoint change.

The system can provide summary views for identifying system metrics such as the top ten best performing thermostats/zones in terms of setpoint-zone temperature gap meter or any other performance metric. The list can be based on best efficiency, closest to setpoint, tenant comfort, and mechanical wear.

The system can also identify the top 10 worst performing thermostats/zones in terms of setpoint-zone temperature gap meter or any other performance metric. The worst performing may be based on worst efficiency, largest setpoint delta, high number of manual setpoint changes, fighting zones, cross-zone influence, or oscillating temperatures. The largest gap between setpoint and zone temperature can be used to identify the worst performing thermostat or zone. The longest delay from zone temperature to setpoint can be used in determining the thermostat or zone which takes the longest time to reach the setpoint. The highest/lowest setpoint can be used to quickly scan the overall zone behavior in the building.

6.14 Method to Determine Operational Statistics

The system can be used to aggregate different views on various operation statistics (per building/zone/thermostat and per occupied/unoccupied). Statistical analysis can be used to identify anomalous behaviors, pressure, temperature, zone-to-zone correlation and zone response. The system can be used to determine total occupied/unoccupied hours. Monthly/Weekly/Daily occupancy analysis will be an overall performance metric.

The system can be used to determine total manual setpoint change attempts.

Data collected on the number of times the tenant tries to change the setpoint will give a good measure for comfort level. The system can be used to determine setpoint change frequency by determining higher manual/scheduled setpoint change frequency to identify any misconfiguration issues. The system can be used to set occupancy alarms and to determine the frequency of occupancy alarms which would indicate a misconfigured schedule.

The system can be used to determine and identify schedule or setpoint anomalies, and to set temperature alarms and possible system fault notifications. The system can also be used to monitor setpoint distribution among buildings/zones, and generate a setpoint-zone temperature gap meter (tracking performance index). The measurement tracking closeness of the setpoint and the zone temperature can be a leading performance index of the system.

6.15 Additional Refinements to the Methods

The system can refine the methods described herein by incorporating information for several other types of sensors such as light/humidity/occupancy, etc. These sensors can be used to augment a WPT system, or can be used as a stand-alone diagnostics/analytics system. External sensor inputs could be used to augment occupancy schedules. Based on motion, light or other passive inputs, the system could sense movement or occupancy and update the system's setpoint schedule without the user's interactions. Energy savings can be realized primarily for zones set to an occupied state, but which do not contain any people.

In one embodiment, an external temperature input could be used to pre-heat or pre-cool the building based on the scheduled temperatures. Outside temperatures could be used to compensate in zones that are influenced by outdoor temperatures. For example, offices with external-facing walls and lobbies would have different influences from outside environmental conditions.

Ambient light-level sensors could be a predictor of a zone's predisposition for external heat loading. Information could be used to adjust the cooling control loop for greater tenant comfort. Remotely-targeted infrared sensors can be used to monitor HVAC vents from a distance. These sensors could be part of the wall-mounted thermostat or standalone. Multiple vent temperatures could be targeted from one sensor location.

Compressor power consumption sensors can determine if a compressor is operating normally or if it is low on oil. Additional sensors can also monitor compressor cycling directly, instead of only observing minor pressure fluctuations in the main pressure line. Additional sensors can also determine if the compressor is appropriately sized for the building, since the WPTs will know the approximate flow-rate of all WPT valves at any given time. If the compressor is cycling excessively while the WPTs are using low flow rates, then there is either a leak or the compressor is undersized. Additional sensors can be used to determine if a compressor is overheating by adding a wireless temperature sensor/probe. A wireless or wired temperature probe can be added to the compressor to monitor its health (oil level/ condition, etc.). Additional sensors can be used to monitor the compressor for oil leaks. Optical sensors can be added in the WPT to detect any foreign substance in the main air line. Chemical/biological contamination sensors can also be added to detect unsafe levels of contaminants. Additionally a dedicated wired/wireless sensor can be added to the tubing at the output of the compressor. Additional sensors can be added to the compressor condensate drain valve to ensure it is periodically cycled. Sensors can be added to monitor the condensate level in the air tank to ensure it does not rise beyond a certain level.

The system may determine air dryer malfunction by adding a humidity sensor. A humidity sensor can be added to all or a select number of WPTs to monitor the humidity level of the compressed air. A humidity sensor can also add a dedicated sensor at the output of the air dryer.

The system can also monitor boiler, chiller, and blower activity by adding a current sensor, or monitor BACnet points from a building's automation system to determine activity of the main units. If the system detects that the main boiler, chiller, and blowers are not operating (when they are shut off overnight or on weekends), an alert can be generated. This information can also be used to properly diagnose system behavior during that time (to avoid incorrect conclusions). An additional use of this information is to tell all WPTs to go to full-closed, so that no airflow is wasted, which would cause the compressor to cycle unnecessarily during that period.

The WPT (or similar devices/sensors) can be used to augment fire detection systems. If a rapid change in temperature is detected at one or more thermostats, an immediate alarm can be triggered in the event that the normal building fire system is slow to respond or malfunctions. This is a "free" incremental benefit enabled by installing WPTs to replace legacy mechanical thermostats.

As noted above, WPT embodiments may include a mechanical controller and a self-contained power section. Such a mechanical controller may be compatible with existing fittings at a site. Further, because a WPT device may have a self-contained power section, WPT device embodiments may be installed in lieu of existing mechanical pneumatic thermostats without having to rewire the site to provide a power supply input.

Embodiments of the present invention, described herein, include various operations. These operations may be performed by hardware components, software, firmware, or a combination thereof. As used herein, the term "coupled to" may mean coupled directly or indirectly through one or more intervening components. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Certain embodiments may be implemented as a computer program product that may include instructions stored on a computer-readable medium. These instructions may be used to program a general-purpose or special-purpose processor to perform the described operations. A computer-readable medium includes any mechanism for storing or transmitting information in a form (e.g., software, processing application) readable by a machine (e.g., a computer). The computer-readable storage medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory, or another type of medium suitable for storing electronic instructions. The computer-readable transmission medium includes, but is not limited to, electrical, optical, acoustical, or any other form of propagated signal (e.g., carrier waves, infrared signals, digital signals, or the like), or another type of medium suitable for transmitting electronic instructions.

Additionally, some embodiments may be practiced in distributed computing environments where the computer-readable medium is stored on and/or executed by more than one computer system. In addition, the information transferred between computer systems may either be pulled or pushed across the transmission medium connecting the computer systems.

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein. Moreover, the applicants expressly do not intend the following claims "and the embodiments in the specification to be strictly coextensive." *Phillips v. AHW Corp.*, 415 F.3d 1303, 1323 (Fed. Cir. 2005) (en banc).

The invention claimed is:

1. An HVAC system comprising:
   at least one pneumatic thermostat having a throttle slope, a pressure sensor on a branch pressure line and an ambient temperature sensor; and
   a processor connected to the pressure sensor and the temperature sensor, the processor configured to perform the following steps:
   a. recording an ambient room temperature from the temperature sensor;
   b. recording a branch line pressure from the pressure sensor;
   c. recording a setpoint value;
   d. changing the setpoint value to a different value;
   e. repeating steps a through d for a plurality of setpoints values;
   f. for each setpoint value in the plurality, calculating an expected pressure based on the recorded setpoint value, the throttle slope and the recorded ambient room temperature;
   g. for each setpoint value in the plurality, analyzing the difference between the expected pressure and the recorded pressure in order to determine if the system is behaving as expected; and h. when the system is not behaving as expected, signaling an alert and compensating for the unexpected behavior.

2. The system of claim 1, wherein step (g) further comprises determining a first trend in the recorded pressures at various recorded ambient temperatures; and determining a second trend in expected pressures at various recorded ambient temperatures, wherein the thermostat is identified as having an incorrect control action when the first trend is substantially opposite to the second trend.

3. The system of claim 1, wherein step (g) further comprises setting a throttle slope tolerance, and determining a recorded pressure slope based on the recorded pressures, wherein the thermostat is identified as having an errant throttle slope when the recorded pressure slope falls outside of the tolerance.

4. The system of claim 1, wherein the HVAC system further comprises at least one actuator on the branch pressure line, and wherein step (g) further comprises:
   setting an ambient temperature error tolerance;
   setting a throttle slope error tolerance, and determining a recorded pressure slope based on the recorded pressures; and
   wherein step (h) further comprises:
      identifying a stuck actuator when both of the following occurs:
         the recorded ambient temperatures differ from the recorded setpoint values by more than the ambient temperature error tolerance; and
         the recorded pressure slope falls within the throttle slope error tolerance.

5. The system of claim 1, wherein step (h) further comprises calculating compensation commands to correct the unexpected behavior.

6. The system of claim 5, wherein the compensation commands are new setpoint values.

7. A non-transitory computer usable medium having computer readable program code embodied therein for self-diagnosing an HVAC system having at least one pneumatic thermostat having a throttle slope, a pressure sensor on a branch pressure line and an ambient temperature sensor, the computer readable code comprising instructions for:
   a. recording an ambient room temperature from the temperature sensor;
   b. recording a branch line pressure from the pressure sensor;
   c. recording a setpoint value;
   d. changing the setpoint value to a different value;
   e. repeating steps a through d for a plurality of setpoints values;
   f. for each setpoint value in the plurality, calculating an expected pressure based on the recorded setpoint value, the throttle slope and the recorded ambient room temperature;
   g. for each set point value in the plurality, analyzing the difference between the expected pressure and the recorded pressure in order to determine if the system is behaving as expected; and
   h. when the system is not behaving as expected, signaling an alert and compensating for the unexpected behavior.

8. The non-transitory computer usable medium of claim 7, wherein step (g) further comprises determining a first trend in the recorded pressures at various recorded ambient temperatures; and determining a second trend in expected pressures at various recorded ambient temperatures, wherein the thermostat is identified as having an incorrect control action when the first trend is substantially opposite to the second trend.

9. The non-transitory computer usable medium of claim 7, wherein step (g) further comprises setting a throttle slope tolerance, and determining a recorded pressure slope based on the recorded pressures, wherein the thermostat is identified as having an errant throttle slope when the recorded pressure slope falls outside of the tolerance.

10. The non-transitory computer usable medium of claim 7, wherein the HVAC system further comprises at least one actuator on the branch pressure line, and wherein step (g) further comprises:
    setting an ambient temperature error tolerance;
    setting a throttle slope error tolerance, and determining a recorded pressure slope based on the recorded pressures; and
    wherein step (h) further comprises:
       identifying a stuck actuator when both of the following occurs:
          the recorded ambient temperatures differ from the recorded setpoint values by more than the ambient temperature error tolerance; and
          the recorded pressure slope falls within the throttle slope error tolerance.

11. The non-transitory computer usable medium of claim 7, wherein step (h) further comprises calculating compensation commands to correct the unexpected behavior.

12. The non-transitory computer usable medium of claim 11, wherein the compensation commands are new setpoint values.

13. A method for self-diagnosing an HVAC system having at least one pneumatic thermostat having a throttle slope, a pressure sensor on a branch pressure line and an ambient temperature sensor, the method comprising:
    a. recording an ambient room temperature from the temperature sensor;
    b. recording a branch line pressure from the pressure sensor;
    c. recording a setpoint value;
    d. changing the setpoint value to a different value;
    e. repeating steps a through d for a plurality of setpoints values;
    f. for each setpoint value in the plurality, calculating an expected pressure based on the recorded setpoint value, the throttle slope and the recorded ambient room temperature;
    g. for each setpoint value in the plurality, analyzing the difference between the expected pressure and the recorded pressure in order to determine if the system is behaving as expected; and
    h. when the system is not behaving as expected, signaling an alert and compensating for the unexpected behavior.

14. The method of claim 13, wherein step (g) further comprises determining a first trend in the recorded pressures at various recorded ambient temperatures; and determining a second trend in expected pressures at various recorded ambient temperatures, wherein the thermostat is identified as having an incorrect control action when the first trend is substantially opposite to the second trend.

15. The method of claim 13, wherein step (g) further comprises setting a throttle slope tolerance, and determining a recorded pressure slope based on the recorded pressures, wherein the thermostat is identified as having an errant throttle slope when the recorded pressure slope falls outside of the tolerance.

16. The method of claim 13, wherein the HVAC system further comprises at least one actuator on the branch pressure line, and wherein step (g) further comprises:
  setting an ambient temperature error tolerance;
  setting a throttle slope error tolerance, and determining a recorded pressure slope based on the recorded pressures; and
wherein step (h) further comprises:
  identifying a stuck actuator when both of the following occurs:
    the recorded ambient temperatures differ from the recorded setpoint values by more than the ambient temperature error tolerance; and
    the recorded pressure slope falls within the throttle slope error tolerance.

17. The method of claim 13, wherein step (h) further comprises calculating compensation commands to correct the unexpected behavior.

18. The method of claim 17, wherein the compensation commands are new setpoint values.

* * * * *